(12) United States Patent
Chang

(10) Patent No.: US 10,632,310 B2
(45) Date of Patent: Apr. 28, 2020

(54) ELECTRONIC STIMULATION DEVICE, METHOD OF TREATMENT AND ELECTRONIC STIMULATION SYSTEM

(71) Applicant: GiMer Medical Co., Ltd., New Taipei (TW)

(72) Inventor: Chi-Heng Chang, New Taipei (TW)

(73) Assignee: GIMER MEDICAL CO., LTD., New Taipei (TW)

( * ) Notice: Subject to any disclaimer, the term of this patent is extended or adjusted under 35 U.S.C. 154(b) by 0 days.

(21) Appl. No.: 15/867,548

(22) Filed: Jan. 10, 2018

(65) Prior Publication Data
US 2018/0126164 A1   May 10, 2018

Related U.S. Application Data

(63) Continuation-in-part of application No. 14/925,379, filed on Oct. 28, 2015, now Pat. No. 10,086,201.
(Continued)

(51) Int. Cl.
*A61N 1/36* (2006.01)
*A61N 1/04* (2006.01)
(Continued)

(52) U.S. Cl.
CPC ....... *A61N 1/36071* (2013.01); *A61N 1/0456* (2013.01); *A61N 1/3616* (2013.01);
(Continued)

(58) Field of Classification Search
CPC .............. A61N 1/36071; A61N 1/3616; A61N 1/36062; A61N 1/0551; A61N 1/36171
See application file for complete search history.

(56) References Cited

U.S. PATENT DOCUMENTS

| 4,398,537 A | 8/1983 | Holmbo |
|---|---|---|
| 6,246,912 B1 | 6/2001 | Sluijter |

(Continued)

FOREIGN PATENT DOCUMENTS

| CN | 1138829 A | 12/1996 |
|---|---|---|
| CN | 101610810 A | 12/2009 |

(Continued)

OTHER PUBLICATIONS

Shechter et al., "Conventional and Kilohertz-frequency Spinal Cord Stimulation Produces Intensity- and Frequency-dependent Inhibition of Mechanical Hypersensitivity in a Rat Model of Neuropathic Pain," Anesthesiology, Aug. 2013, 119(2): pp. 422-432.
(Continued)

*Primary Examiner* — Allen Porter
*Assistant Examiner* — Natasha Patel
(74) *Attorney, Agent, or Firm* — Muncy, Geissler, Olds & Lowe, PC

(57) ABSTRACT

An electronic stimulation device is adapted for electrically stimulating a target zone of an organism. The electronic stimulation device comprises at least one electronic stimulation unit. The electronic stimulation unit includes at least one first electrode and at least one second electrode. The electronic stimulation unit receives an electrical stimulation signal to impel the first electrode and the second electrode to generate an electric field. The range of the electric field covers the target zone, and the electric field strength ranges from 100 V/m to 1000 V/m. The target zone is selected from the group consisting of a dorsal root and a dorsal root entry zone of a spinal cord, and the electronic stimulation unit is configured to be disposed in an anatomical space of the organism, and said anatomical space is selected from the group consisting of a spinal canal, a lateral recess and an epidural space.

24 Claims, 30 Drawing Sheets

Related U.S. Application Data which is a continuation-in-part of application No. 14/049,235, filed on Oct. 9, 2013, now Pat. No. 9,526,889.

(51) Int. Cl.
  *A61N 1/06* (2006.01)
  *A61N 1/05* (2006.01)

(52) U.S. Cl.
  CPC ........ *A61N 1/36062* (2017.08); *A61N 1/0551* (2013.01); *A61N 1/06* (2013.01); *A61N 1/36171* (2013.01)

(56) References Cited

U.S. PATENT DOCUMENTS

| | | |
|---|---|---|
| 7,162,303 B2 | 1/2007 | Levin et al. |
| 7,330,762 B2 | 2/2008 | Boveja et al. |
| 7,337,006 B2 | 2/2008 | Kim et al. |
| 7,447,546 B2 | 11/2008 | Kim et al. |
| 7,450,993 B2 | 11/2008 | Kim et al. |
| 7,502,651 B2 | 3/2009 | Kim et al. |
| 7,580,753 B2 | 8/2009 | Kim et al. |
| 7,647,115 B2 | 1/2010 | Levin et al. |
| 8,082,039 B2 | 12/2011 | Kim et al. |
| 8,131,372 B2 | 3/2012 | Levin et al. |
| 8,170,675 B2 | 5/2012 | Alataris et al. |
| 8,209,021 B2 | 6/2012 | Alataris et al. |
| 8,229,565 B2 | 7/2012 | Kim et al. |
| 8,249,701 B2 | 8/2012 | Imran et al. |
| 8,255,057 B2 | 8/2012 | Fang et al. |
| 8,311,639 B2 | 11/2012 | Parker et al. |
| 8,355,792 B2 | 1/2013 | Alataris et al. |
| 8,355,797 B2 | 1/2013 | Caparso et al. |
| 8,359,102 B2 | 1/2013 | Alataris et al. |
| 8,359,103 B2 | 1/2013 | Alataris et al. |
| 8,380,318 B2 | 2/2013 | Kishawi et al. |
| 8,396,559 B2 | 3/2013 | Alataris et al. |
| 8,423,147 B2 | 4/2013 | Alataris et al. |
| 8,428,748 B2 | 4/2013 | Alataris et al. |
| 8,457,759 B2 | 6/2013 | Parker et al. |
| 8,498,710 B2 | 7/2013 | Walker et al. |
| 8,509,905 B2 | 8/2013 | Alataris et al. |
| 8,509,906 B2 | 8/2013 | Walker et al. |
| 8,768,472 B2 | 7/2014 | Fang et al. |
| 9,764,137 B2 | 9/2017 | Lin et al. |
| 9,770,592 B2 | 9/2017 | Lin et al. |
| 2001/0007949 A1 | 7/2001 | Silverstone |
| 2004/0162590 A1 | 8/2004 | Whitehurst et al. |
| 2005/0154425 A1 | 7/2005 | Boveja et al. |
| 2006/0085056 A1 | 4/2006 | Schouenborg |
| 2006/0116721 A1 | 6/2006 | Yun et al. |
| 2006/0149337 A1 | 7/2006 | John |
| 2007/0021803 A1 | 1/2007 | Deem et al. |
| 2007/0129760 A1 | 6/2007 | Demarais |
| 2009/0062886 A1 | 3/2009 | O'Handley et al. |
| 2009/0093858 A1 | 4/2009 | Diubaldi |
| 2009/0204193 A1* | 8/2009 | Kokones ............... A61N 1/0529 607/116 |
| 2009/0270943 A1 | 10/2009 | Maschino |
| 2010/0010567 A1 | 1/2010 | Deem et al. |
| 2010/0137938 A1 | 6/2010 | Kishawi |
| 2010/0152811 A1 | 6/2010 | Flaherty |
| 2010/0298905 A1 | 11/2010 | Simon |
| 2011/0130804 A1 | 6/2011 | Lin et al. |
| 2011/0137381 A1* | 6/2011 | Lee .................. A61N 1/0529 607/62 |
| 2012/0029591 A1 | 2/2012 | Simon et al. |
| 2012/0035687 A1 | 2/2012 | Lu et al. |
| 2012/0245652 A1 | 9/2012 | Whitehurst et al. |
| 2012/0296389 A1 | 11/2012 | Fang et al. |
| 2012/0310140 A1* | 12/2012 | Kramer ............... A61K 9/0009 604/20 |
| 2013/0079862 A1 | 3/2013 | Ellrich |
| 2013/0096643 A1 | 4/2013 | Fang et al. |
| 2013/0116752 A1 | 5/2013 | Parker et al. |
| 2013/0138178 A1 | 5/2013 | Lin et al. |
| 2013/0144359 A1 | 6/2013 | Kishawi et al. |
| 2013/0317564 A1 | 11/2013 | Lin et al. |
| 2014/0039579 A1 | 2/2014 | Mashiach et al. |
| 2014/0257437 A1 | 9/2014 | Simon et al. |
| 2015/0100112 A1 | 4/2015 | Chang et al. |
| 2016/0045735 A1* | 2/2016 | Chang .................. A61N 1/0551 607/46 |
| 2016/0096022 A1 | 4/2016 | Lin et al. |
| 2016/0263377 A1 | 9/2016 | Lin et al. |
| 2016/0263378 A1 | 9/2016 | Lin et al. |
| 2017/0043163 A1 | 2/2017 | Lin et al. |
| 2017/0056661 A1 | 3/2017 | Lin et al. |

FOREIGN PATENT DOCUMENTS

| | | |
|---|---|---|
| CN | 102120060 A | 7/2011 |
| CN | 102202729 A | 9/2011 |
| CN | 102939066 A | 2/2013 |
| TW | M498025 U | 4/2015 |
| WO | WO 95/19804 | 7/1995 |
| WO | WO 2008/094345 A1 | 8/2008 |

OTHER PUBLICATIONS

Lin et al., "The effect of high and low frequency electroacupuncture in pain after lower abdominal surgery," Pain, 99 (2002), pp. 509-514.

Wen et al., "A minimal stress model for the assessment of electroacupuncture analgesia in rats under halothane," European Journal of Pain, 11 (2007), pp. 733-742.

Zhuang et al., "Role of the CX3CR1/p38 MAPK pathway in spinal microglia for the development of neuropathic pain following nerve injury-induced cleavage of fractalkine," Brain Behav Immun., 21(5), Jul. 2007, pp. 642-651.

Wen et al., "Nerve conduction blockade in the sciatic nerve prevents but does not reverse the activation of p38 mitogen-activated protein kinase in spinal microglia in the rat spared nerve injury model," Anesthesiology, 107 (2007), pp. 312-321.

Shieh et al., "A novel fuzzy pain demand index derived from patient-controlled analgesia for postoperative pain," IEEE Transactions on Biomedical Engineering, vol. 54, No. 12, Dec. 2007, pp. 2123-2132.

Shieh et al., Fuzzy Logic: Theory, Programming and Applications, 1$^{st}$ edition, Chapter 7, "Fuzzy logic applied in multidimensional model of postoperative pain derived from patient-controlled analgesia," published by Nova Science Publishers, Jun. 2009, pp. 247-267.

Chiu et al., "Pain control on demand based on pulsed radiofrequency stimulation of the dorsal root ganglion using a batteryless implantable CMOS SoC," IEEE Transactions on Biomedical Circuits and Systems, vol. 4, No. 6, Dec. 2010, pp. 350-359.

Lin et al., IEEE International Solid State Circuits Conference, "ISSCC 2010/Session 12/Emerging Medical Applications/12.1," Feb. 7-11, 2010, pp. 234-236.

Wen et al., "DNIC—mediated analgesia produced by a supramaximal electrical or a high-dose formalin conditioning stimulus: roles of opioid and α2-adrenergic receptors," Journal of Biomedical Science, 17:19, 2010, pp. 1-13.

Yeh et al., "A novel continuous visual analog scale model derived from pain-relief demand index via Hilbert Huang transform for postoperative pain," Journal of Medical and Biological Engineering, 31(3), Jan. 2011, pp. 169-176.

Chang et al., "Feasibility Study of Implantable Pulsed-Radiofrequency Stimulator with Verification on Sciatica Rat Model," Institute of Biomedical Engineering National Taiwan University, 2009, 2 pages.

Barry Coburn et al., "A Theoretical Study of Epidural Electrical Stimulation of the Spinal Cord—Part I: Finite Element Analysis of

(56) References Cited

OTHER PUBLICATIONS

Stimulus Fields," IEEE Transactions on Biomedical Engineering, vol. BME-32, No. 11, Nov. 1985, pp. 971-977.

* cited by examiner

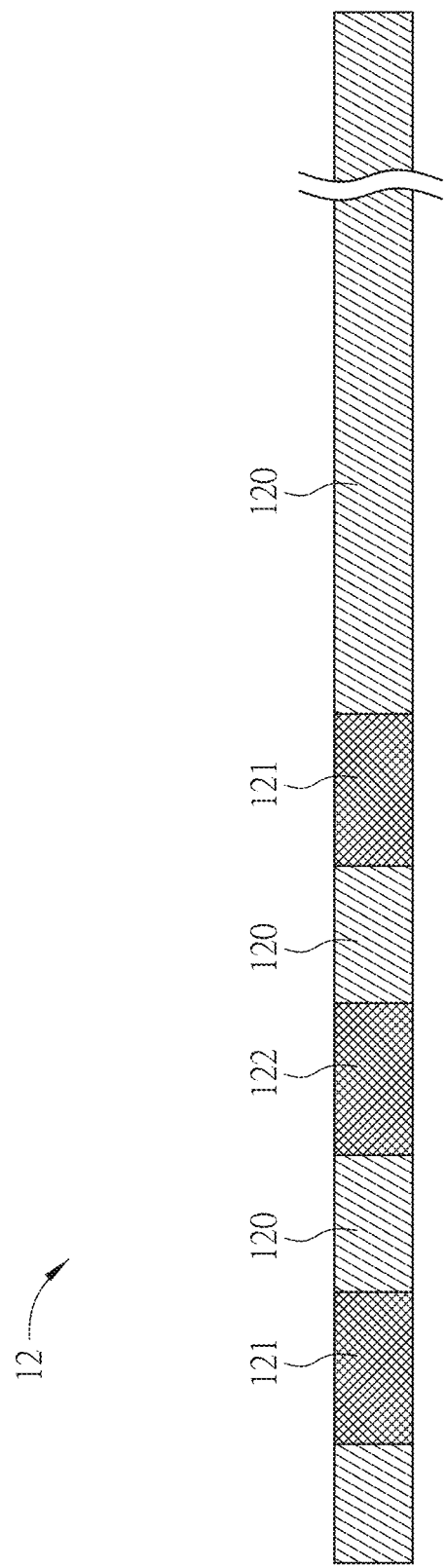

ELECTRONIC STIMULATION DEVICE, METHOD OF TREATMENT AND ELECTRONIC STIMULATION SYSTEM

CROSS REFERENCE TO RELATED APPLICATIONS

This application is a Continuation-In-Part of co-pending application Ser. No. 14/925,379 filed on Oct. 28, 2015, which is a Continuation-In-Part of application Ser. No. 14/049,235 filed on Oct. 9, 2013, which issued as U.S. Pat. No. 9,526,889 on Dec. 27, 2016, for which priority is claimed under 35 U.S.C. § 120; the entire contents of which are hereby incorporated by reference.

BACKGROUND

Technical Field

The invention relates to an electronic stimulation device, in particular to an electronic stimulation device for electrically stimulating a target zone of an organism without generating paresthesia.

Related Art

The human nerve system provides transmission paths for the commands issued from the brain. The human nerve has a threshold and the threshold is often reduced around a damaged spot of the nerve. Therefore, uncomfortable pain or ache is frequently and easily felt at this spot. After a period of time, this spot would become a source of chronic pain.

Clinically, an approach called Continuous Radiofrequency (CRF) or Radiofrequency Ablation is widely applied to ease various nerve pains. The approach inserts a pin into the proximity of related nerve tissue, applies continuous high-frequency signal to create high temperature so as to destroy the nerve tissue, thereby alleviating the nerve pain. However, due to the human body's self-repair function, the destroyed nerve tissue will try to heal itself. When this happens, newly developed tissue grows randomly on the destroyed tissue, and it is quite common that a neuroma is formed. The neuroma, once formed, often oppresses the nerve system and causes even more serious pain.

SUMMARY

An electronic stimulation device is adapted for electrically stimulating a target zone of an organism. The electronic stimulation device comprises at least one electronic stimulation unit. The electronic stimulation unit includes at least one first electrode and at least one second electrode. The electronic stimulation unit receives an electrical stimulation signal to impel the first electrode and the second electrode to generate an electric field. The range of the electric field covers the target zone, and the electric field strength ranges from 100 V/m to 1000 V/m. At least part of the electronic stimulation unit is configured to be disposed in a lateral recess.

A method of treatment is applied to electrically stimulate a target zone of an organism by a stimulation device. The stimulation device includes an electronic stimulation unit including at least one first electrode and at least one second electrode. The method comprises: implanting at least part of the electronic stimulation unit in a lateral recess of the organism; delivering an electrical stimulation signal by the electronic stimulation unit; generating an electric field covering the target zone by the first electrode and the second electrode, wherein the electric field strength ranges from 100 V/m to 1000 V/m; and electrically stimulating the target zone.

An electronic stimulation system comprises a control unit and an electronic stimulation device. The electronic stimulation device comprises at least one electronic stimulation unit including at least one first electrode and at least one second electrode. The controller directs the electronic stimulation unit to deliver an electrical stimulation signal to impel the first electrode and the second electrode to generate an electric field. The range of the electric field covers the target zone and the electric field strength ranges from 100 V/m to 1000 V/m for electrically stimulating the target zone. At least part of the electronic stimulation unit is configured to be disposed in a lateral recess.

In one embodiment, the electrical stimulation signal is a pulse signal and its pulse frequency ranges from 0 to 1 KHz.

In one embodiment, the frequency of the electrical stimulation signal ranges from 200 KHz to 1000 KHz.

In one embodiment, the voltage of the electrical stimulation signal ranges from −10V to −1V or ranges from 1V to 10V.

In one embodiment, the current of the electrical stimulation signal ranges from 2 mA to 50 mA.

In one embodiment, the distance from the first electrode to the second electrode ranges from 1 mm to 7 mm, and the distance between the first electrode, the second electrode and the target zone ranges from 0 to 10 mm.

In one embodiment, the electrical stimulation signal is adapted to block the neurotransmission in the target zone.

In one embodiment, the target zone is brain, vertebral column, dorsal root ganglion and/or spinal dorsal horn.

In one embodiment, the electronic stimulation unit receives a test (low-frequency) electrical stimulation signal, and the frequency of the test electrical stimulation signal is less than 1 KHz.

In one embodiment, the electronic stimulation unit comprises a plurality of subunits and each subunit comprises at least one first electrode and at least one second electrode.

In one embodiment, in each subunit the first electrode is separated from the second electrode with a first distance, and each subunit is separated from each other in a second distance, and the first distance is smaller than the second distance.

In one embodiment, the total amount of the subunits is at least three.

In one embodiment, each subunit is configured to be disposed corresponding to one segment of the spine of the organism.

In one embodiment, the target zone is selected from the group consisting of a dorsal root, dorsal horn, spinothalamic tract, Lissauer's tract and a dorsal root entry zone of a spinal cord.

In one embodiment, the electronic stimulation unit comprises a lead including at least one first electrode and at least one second electrode and the distal lead tip is configured to be disposed between T8 and T10.

BRIEF DESCRIPTION OF THE DRAWINGS

The embodiments will become more fully understood from the detailed description and accompanying drawings, which are given for illustration only, and thus are not limitative of the present invention, and wherein:

FIGS. 2A and 2B are enlarged diagrams showing a portion of the electronic stimulation unit in FIG. 1;

DETAILED DESCRIPTION OF THE INVENTION

The embodiments of the invention will be apparent from the following detailed description, which proceeds with reference to the accompanying drawings, wherein the same references relate to the same elements.

Figure 1A:
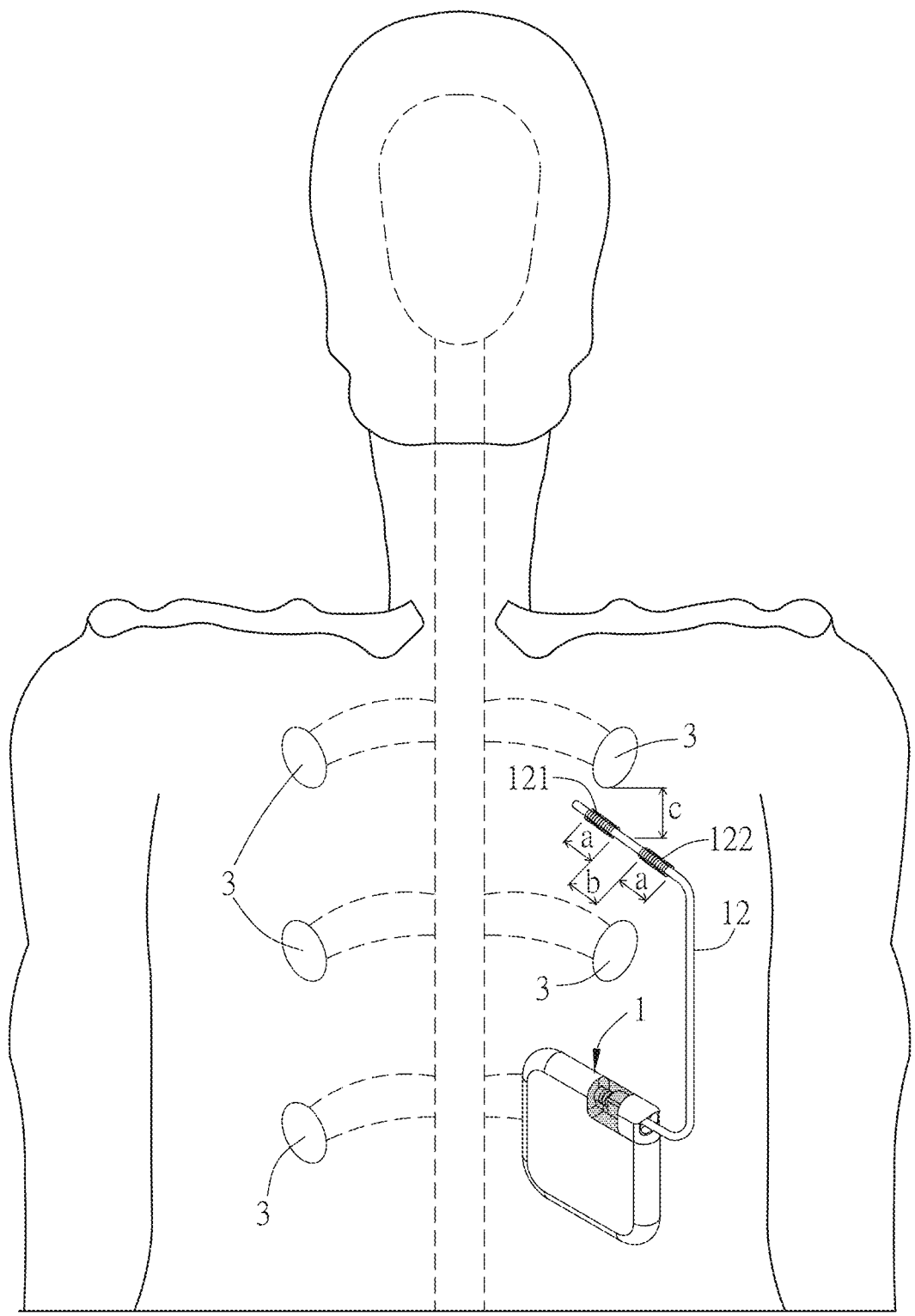
FIG. 1A is a schematic diagram showing the electronic stimulation device applied to the dorsal root ganglion according to the first embodiment.

FIG. 1A is a schematic diagram showing the electronic stimulation device applied to the dorsal root ganglion according to the first embodiment. Referring to FIG. 1A, an electronic stimulation device 1 is applied to electrically stimulate a target zone of an organism. In the embodiment, the target zone is dorsal root ganglion 3 for example. Alternatively, the target zone may be for example but not limited to brain, spinal cord, sympathetic nerve and/or parasympathetic nerve of an organism. The target zone of the spinal cord are ventral root, ventral horn, dorsal root, dorsal root entry zone (DREZ), dorsal root ganglion and/or dorsal horn. The target level of spinal cord may be cervical level, thoracic level, lumbar level, sacral level or caudal level for example. In this embodiment, the target levels of the spinal cord is at T9 and T10 for example. The following paragraphs will describe the elements and applications of the electronic stimulation device 1.

For the sake of clarity regarding the step details of the method, the circuits and interaction of the electronic stimulation device 1 and the controller 2 are explained first in the following paragraphs. Then, the following paragraphs describe electrically stimulating the target zone of the organism by the electronic stimulation device 1 of the embodiment. However, the descriptions in the following embodiments are exemplary but not intended to limit the scope of the invention.

Figure 1B:
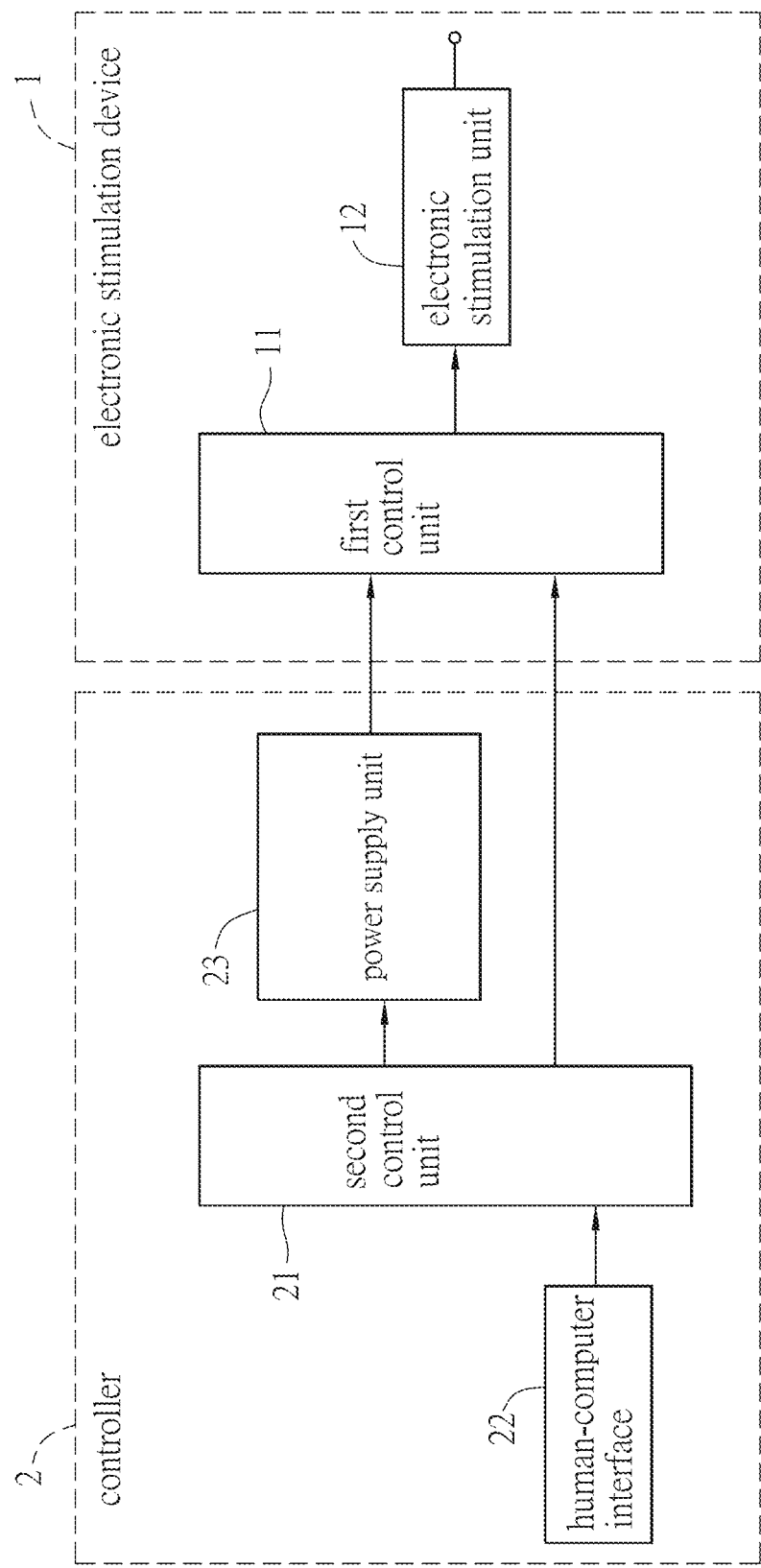
FIG. 1B is a circuit block diagram of the electronic stimulation device and the controller in FIG. 1A.

FIG. 1B is a circuit block diagram of the electronic stimulation device and the controller in FIG. 1A. Referring to FIG. 1B, a controller 2 provides configuration parameters and supplies energy for the electronic stimulation device 1. Because the controller 2 does not need to be implanted in the organism, it may be called the external controller 2. Elements of the electronic stimulation device 1 and the controller 2 and their relationships will be described in the following paragraphs.

In the embodiment, the electronic stimulation device 1 includes a first control unit 11 and an electronic stimulation unit 12. The electronic stimulation unit 12 is coupled to the first control unit 11. The controller 2 includes a second control unit 21, a human-computer interface 22 and a power supply unit 23. The human-computer interface 22 is coupled to the second control unit 21. The power supply unit 23 is also coupled to the second control unit 21 and acts as the power source of the controller 2. The power supply unit 23 may be a battery or a rechargeable battery, or it may be a power adapter connected to mains electricity to supply electrical power.

In the embodiment, the user may use the human-computer interface 22 to operate the controller 2. Before beginning, the system default values of the controller 2 is initialized. Then, he may also use the human-computer interface 22 to input the required configuration parameters to the second control unit 21. In the embodiment, the human-computer interface 22 may be for example but not limited to touch button, touch panel, physical button or their combination. The second control unit 21 instructs the power supply unit 23 to supply DC power to the elements of the electronic stimulation device 1 (for example the electronic stimulation unit 12) to operate.

The first control unit 11 and the second control unit 21 may be implemented with digital circuit such as IC or implemented with analog circuit. For example, IC may be a micro-processor, a MCU, a programmable logic gate array (for example FPGA or CPLD) or ASIC. In the embodiment, it is a MCU for example but not limited thereto.

In the embodiment, the electronic stimulation device 1 is an implantable electronic stimulation device for example. The implantable electronic stimulation device means that at least one portion of the element of the electronic stimulation device 1 is implanted in the individual body (for example: subcutaneous). The first control unit 11 may be defined as an implantable pulse receiver (IPR) including a pulse generating circuit and a power management circuit. In the embodiment, the electronic stimulation unit 12 is adapted to be implanted in the organism. The first control unit 11 may be implanted within the organism or disposed outside the organism depending on actual or design requirement. If the electronic stimulation unit 12 is prepared to be implanted into one organism, it is better to be implanted within the epidural space (especially dorsal side epidural space) or near the dorsal root ganglion of the spinal level corresponding to the patient's pain or symptom. The organism preferably may include mammals such as mouse, human, rabbit, cattle, sheep, pig, monkey, dog, cat, etc. Preferably, it is human. For example, it is human. Moreover, the electronic stimulation device 1 may be changed to a transcutaneous electronic stimulation device depending on the symptom and requirement of the patient.

Figure 2B:
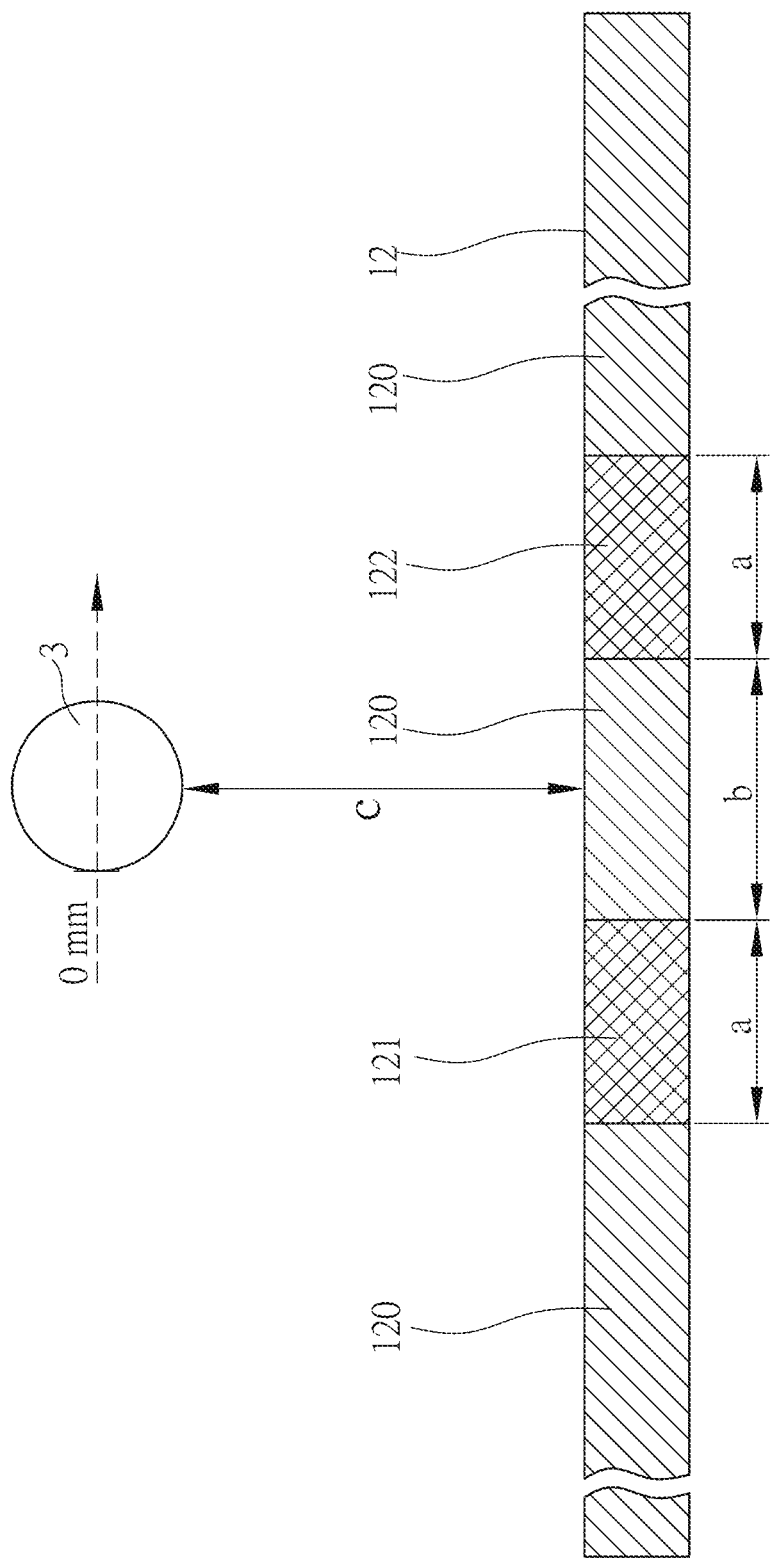

As to the configuration of the electronic stimulation unit 12, referring to FIG. 1A and FIG. 2B, the electronic stimulation unit 12 comprises a flexible lead including at least one first electrode 121 and at least one second electrode 122. In the embodiment, these electrodes are located at the proximal end of the flexible lead and can be classified into work electrodes and reference electrodes, according to the types of electronic signals received by them. The work electrodes and the reference electrodes are disposed staggered, so as to establish a dense electrical field. The quantities of work electrodes can equal to or not equal to that of reference electrodes. At least one electrical stimulation signal generated by the electronic stimulation unit 12 will be delivered to the work electrodes and outwardly to the organism, and the reference electrodes provide the path for the electric current to flow back to the electronic stimulation unit 12. In the present embodiment, the electrical stimulation signal can be a signal of alternating current (AC). Therefore, in a certain instant, the first electrode 121 is functioned as a work electrode whereas the second electrode 122 is functioned as a reference electrode. Later, in a subsequent instant due to the AC configuration, the first electrode 121 then becomes a reference electrode and the second electrode 122 becomes a work electrode. The reference electrodes can be electrically coupled to the ground potential or a DC level of the electronic stimulation device 1. Thus, in an AC configuration, the first electrode 121 and the second electrode 122 may function as the reference electrode to each other. In addition, there are maybe two pairs, three pairs or more than three pairs of electrodes in the electronic stimulation unit 12, and they may be evenly distributed on the lead, namely the electronic stimulation unit 12. The above electrodes operate in biphasic mode to generate an electric field between the first electrode 121 and the second electrode 122. In the embodiment, between the first electrode 121 and the second electrode, there are coils or wires formed from winding coaxial conductor which are electrically connected to the electrodes. For example, the material of the first electrode 121 and the second electrode 122 may be metal for example platinum, silver, gold, iridium and/or other conductive metal. Between the first electrode 121 and the second electrode 122, a zone is defined by the coils or wires which are compactly wound cable electrically connected to the electrodes. The first electrode 121 and the second electrode 122 are disposed at one end of the electronic stimulation unit 12, two contacts 123 acting as the connectors for the work and reference electrodes disposed at the other end of the electronic stimulation unit 12. The two contacts 123 are electrically connected or coupled to the first control unit 11. The first electrode 121, the second electrode 122 are respectively linked to the contacts 123 through the different wires. Besides, the wires of the electronic stimulation unit 12 beyond the first electrode 121 and the second electrode 122 is covered by an insulator 120.

The range of the individual length a of each electrode depends on actual or design requirement. The electrode length a is between 0.5~6 mm, preferably between 1~4 mm. The individual length a of the first electrode 121 and the second electrode 122 means that the length of the electrode in the direction parallel to the extension direction of the major axis of the cable of the electronic stimulation unit 12.

The range of the individual length a of the first electrode 121 and the second electrode 122 depends on actual or design requirement. For example, the length a is between 1~3 mm. The distance b between the first electrode 121 and the second electrode 122 is between 1~7 mm, preferably between 1~4 mm. For example, the distance b of the two adjacent ends of the adjacent first and second electrodes 121, 122 is preferably between 1~4 mm.

A second distance c exists between the first electrode 121 and the second electrode 122 of the electronic stimulation unit 1 and the target zone (dorsal root ganglion) 3. The second interval distance c is defined as the shortest distance from the midpoint of the adjacent first and second electrodes 121, 122 to the target zone 3. In the embodiment, the second interval distance c ranges from 0 to 10 mm, preferably from 0 to 5 mm. If the distance c is 0, the midpoint of the first electrode 121 and the second electrode 122 in the projection direction overlaps the target zone 3.

Figure 1C:
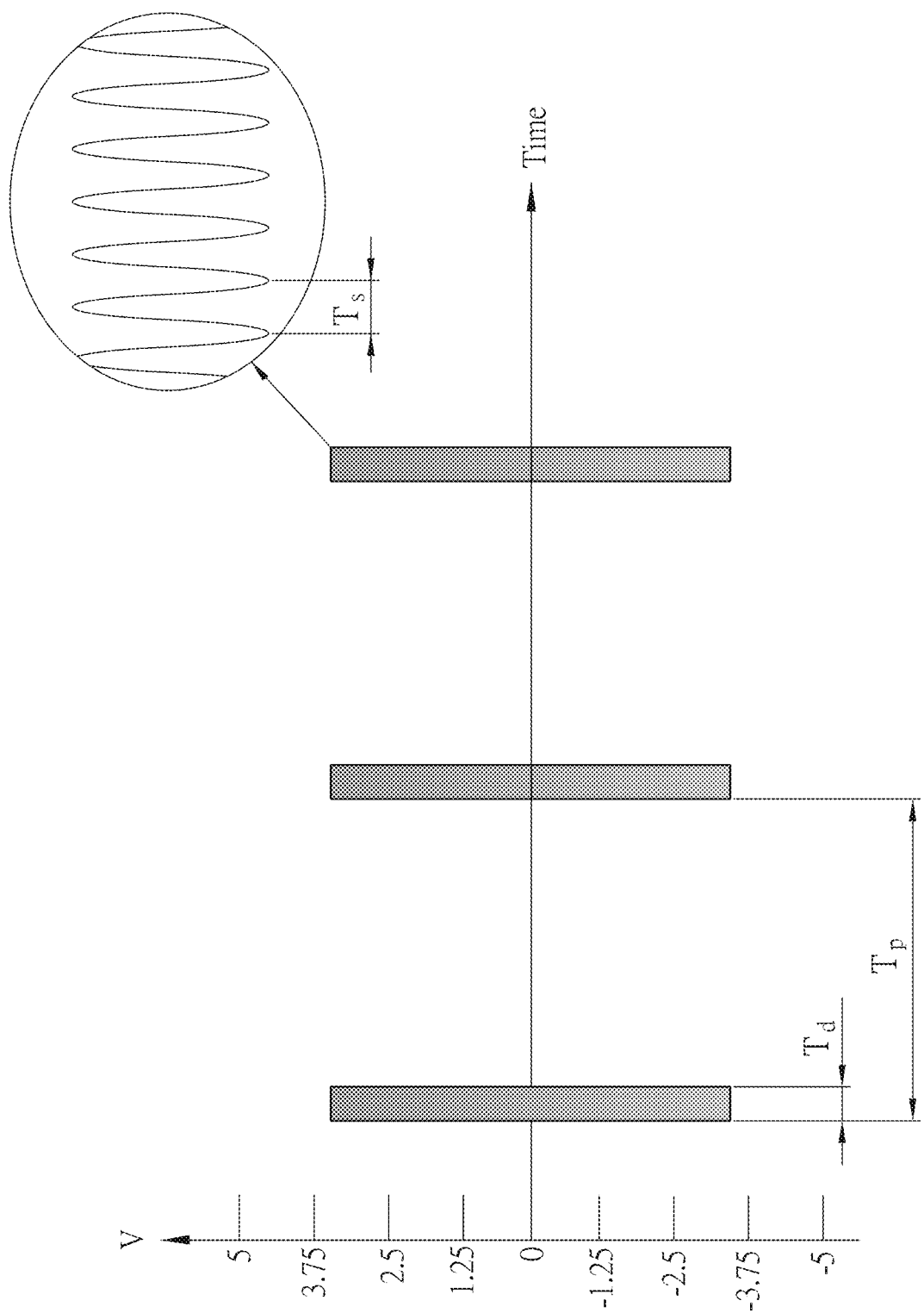
FIG. 1C is a schematic diagram showing the pulse signal of the electrical stimulation signal of the electronic stimulation device in FIG. 1.

Referring to FIG. 1C, in the embodiment, the electrical stimulation signal outputted from the electronic stimulation device 1 may be a continuous sine wave, a continuous triangle wave or an electrical stimulation signal of high-frequency AC pulses. If it is an electrical stimulation pulse signal, one pulse cycle time Tp has a plurality of pulse signals and at least one period of rest time. One pulse cycle time is the reciprocal of pulse repetition frequency. The pulse repetition frequency (also called pulse frequency) is between 0~1 KHz, preferably between 1~100 Hz. In the embodiment, the pulse repetition frequency of the electrical stimulation signal is preferably between 1 Hz to 10 Hz, such as 2 Hz. Besides, the duration time Td of pulses in one pulse cycle time is between 1~250 ms, preferably between 10~100 ms. In the embodiment it is 25 ms for example.

Referring to FIG. 1C, in the embodiment, the electronic stimulation unit 12 is adapted to transmit a first (high-frequency) electrical stimulation signal. For example, the patient, healthcare workers or physicians use the interface of the controller 2 to set the electrical stimulation frequency, stimulation period, stimulation intensity and/or other parameters of the electrical stimulation signal. Then, the controller 2 outputs the parameters and energy to the electronic stimulation device 1, and directs the electronic stimulation unit 1 to output signal via the first control unit 11. In the embodiment, the frequency of the electrical stimulation signal is about 600 KHz. In other words, its stimulation cycle time Ts is about 1.67 μs.

For example, the electronic stimulation device may be chosen to be driven in a constant voltage mode or a constant current mode. The constant voltage mode is safer than the constant current mode, but the intensity in the constant voltage mode is less stable than in the constant current mode. Choosing which mode depends on the target zone to be electrically stimulated. For example, if the target is dorsal column, the constant current mode is chosen. If the target is the dorsal root ganglion, the constant voltage mode is chosen. When the constant voltage mode is chosen for driving, the voltage of the electrical stimulation signal is constant, and the current of the electrical stimulation signal varies with the positions and resistances of the first electrode 121 and the second electrode 122. Otherwise, when the constant current mode is chosen for driving, the current of the electrical stimulation signal is constant, and the voltage of the electrical stimulation signal varies with the positions and resistances of the first electrode 121 and the second electrode 122. For example, in the constant voltage mode, the voltage of the electrical stimulation signal ranges from −10V to −1V or from 1V to 10V. Preferably, the voltage of the electrical stimulation signal ranges from 10V to −3 V or from 3V to 10V. In the constant current mode, the current of the electrical stimulation signal ranges from 2 mA to 50 mA, preferably from 4 ma to 30 mA.

Besides, the frequency of the electrical stimulation signal is between 200 KHZ~1000 KHz, preferably between 200 KHz~250 KHz, 250 KHz~350 KHz, 350 KHz~450 KHz, 450 KHz~550 KHz, 550 KHz~650 KHz, 650 KHz~750 KHz, 750 KHz~800 KHz, or 800 KHz~1000 KHz. If the selected frequency is between 200 KHz~450 KHz, the device operates in relatively low frequency so it is less risky to produce biological heat for better safety. Otherwise, if the selected frequency is between 550 KHz~1000 KHz, the generated electric field has greater density so its electrical stimulation has better performance. In addition, by adjusting the duration time Td, the amount of the electrical stimulation is adjusted and the time for dissipating the produced biological heat accordingly. For example, if the stimulation intensity is relatively low, the duration time Td may be increased to continuously stimulate. If the stimulation intensity and the frequency are relatively high, the duration time Td may be decreased to raise the time for dissipating.

When the electronic stimulation unit 12 receives the electrical stimulation signal, the first electrode 121 and the second electrode 122 of the electronic stimulation unit 12 accordingly generate an electric field. The distance from the first electrode 121 and the second electrode 122 to the target zone 3 is arranged within the range of the second distance c, so the electric field generated by the first electrode 121 and the second electrode 122 covers the target zone 3. In other words, the electric field covers the target zone 3 to electrically stimulate the target zone 3 with low intensity, low temperature and high frequency. Without destroying the neural cells of the target zone 3, the biomolecule generation by the target zone 3 is suppressed, and the threshold of the target zone 3 is also raised. Thus, the neurotransmission capability of the nerve of the target zone 3 is lowered and the neurotransmission is blocked or the nerve of the target zone is desensitized. As a result, the patient feels nerve pain relieved.

Furthermore, the patient may feel as little as possible pain on the target zone without generating relative much sensations of paresthesia (or paresthesia-free) if applying the electronic stimulation device for electrical stimulation. The patient suffering pains over a long period of time may accept this electrical stimulation treatment which is effective and generates as little as possible sensations of paresthesia. Preferably, the treatment resulting from the electrical stimulation by the electronic stimulation device in the embodiment may keep effective at least 24 hours to one week. In other words, the neurotransmission of at least partial nerves of target zone is blocked at least 24 hours to one week. Thus, the patient may decrease the treatment time (duration time) per day or per week, so he may be more possibly willing to receive the treatment. Because the details can refer to the following experimental examples, they are not repeated here.

Figure 3A:
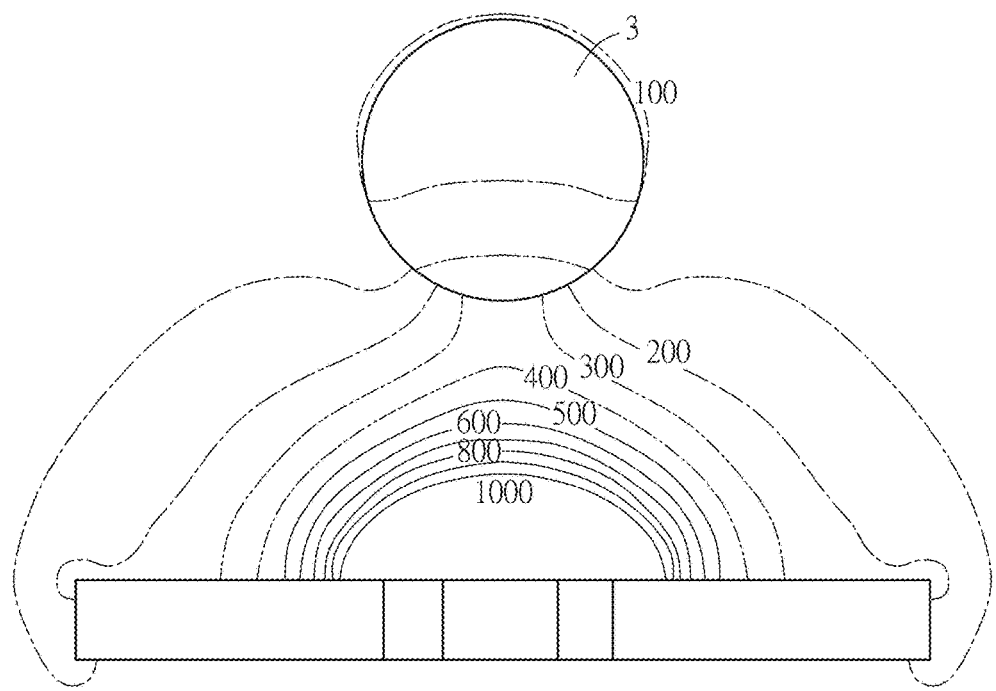
FIG. 3A to 3E and FIG. 4A to 4E are schematic diagrams of the electric field simulation of the electronic stimulation device.
Figure 3B:
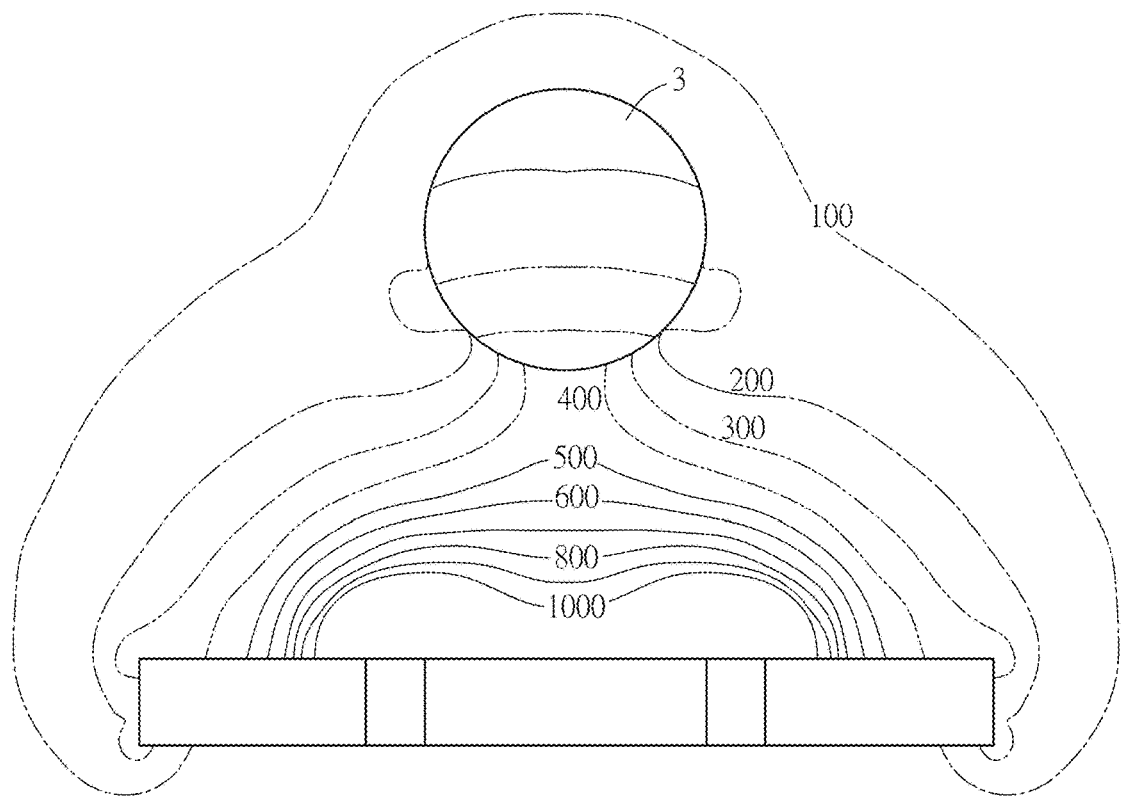
Figure 3C:
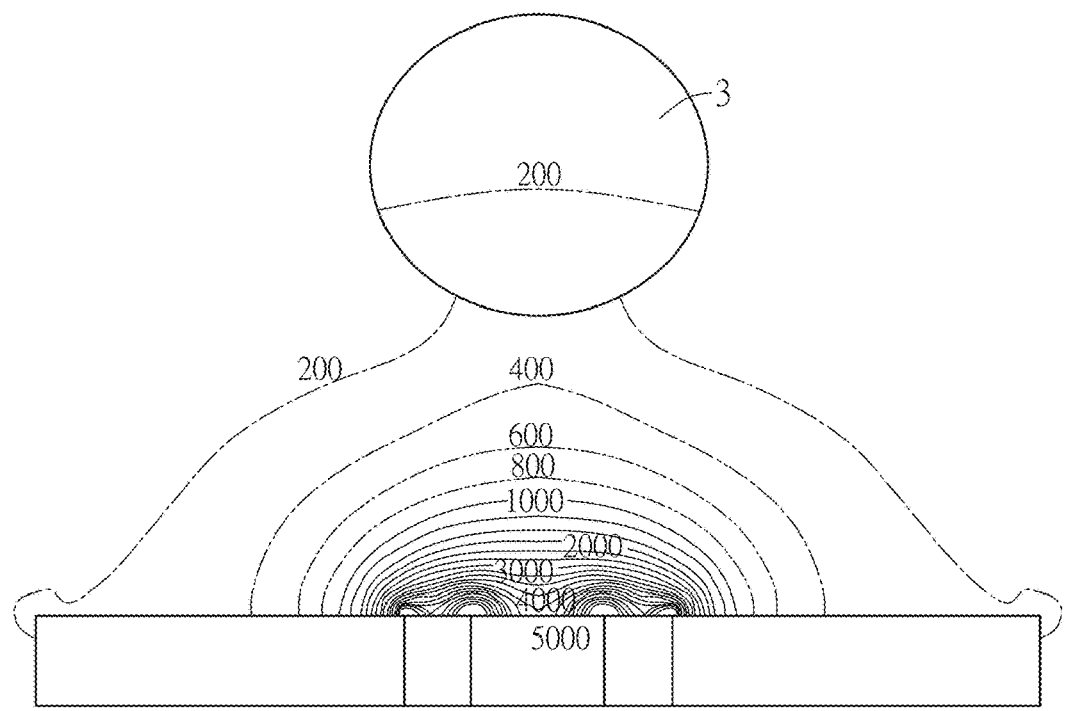
Figure 3D:
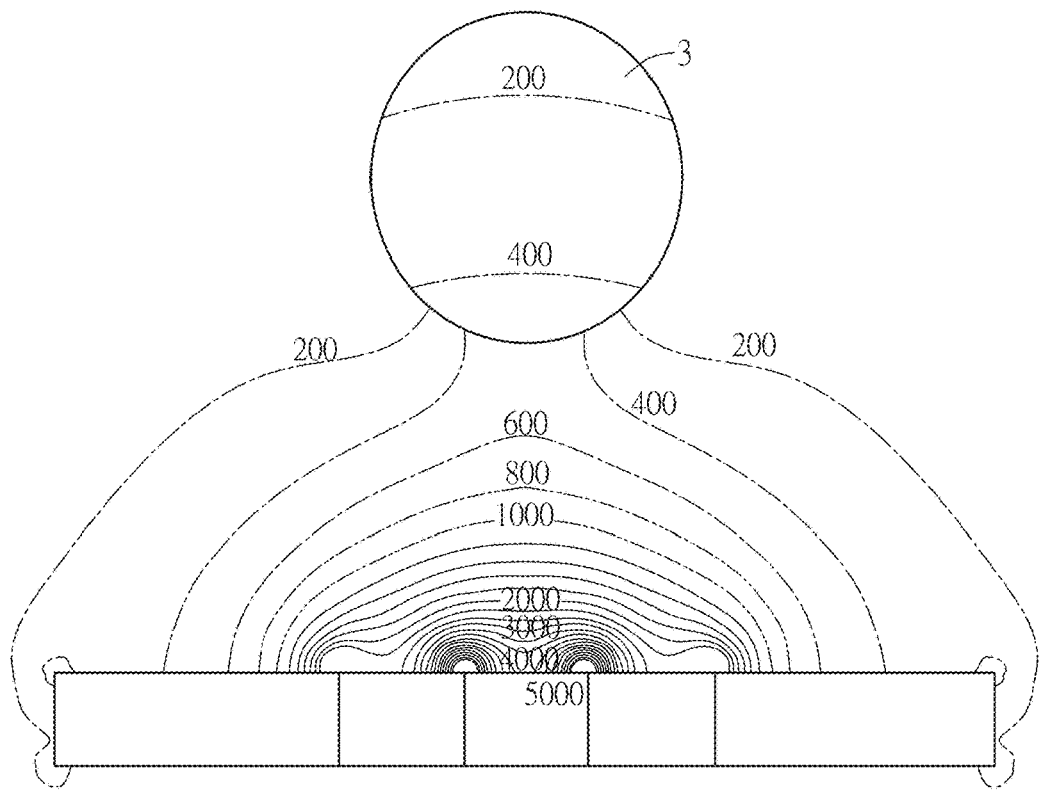
Figure 3E:
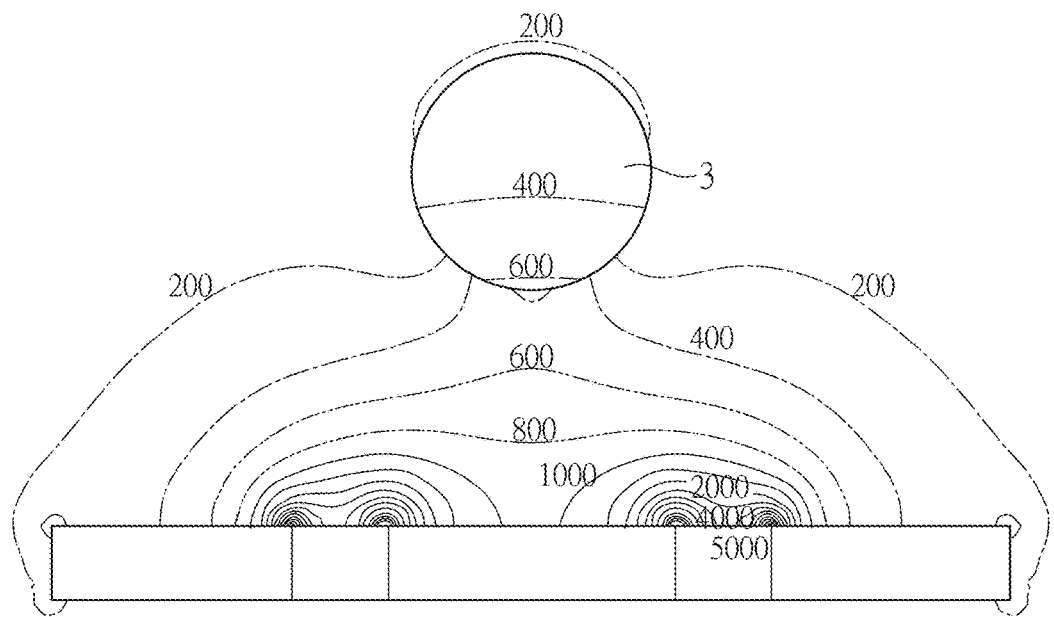

Furthermore, referring to FIG. 3A to FIG. 3D, the field pattern of the electric field is adjusted by adjusting the electrode length a of the first electrode 121 and the second electrode 122, the first interval distance b between the first electrode 121 and the second electrode 122, or the second interval distance c between the first electrode 121, the second electrode 122 and the dorsal root ganglion 3. For example, the voltage of the electrical stimulation signal is 5V, its frequency is 500 KHz, and the distance c is 5 mm. Assuming that the electrode length a and the distance c of the first electrode 121 and the second electrode 122 are constant (a=1 mm, c=5 mm), as smaller the distance b (b=2 mm) between the first electrode 121 and the second electrode 122 as shown in the electric field simulation diagram in FIG. 3, the electric field (the strength of the electric field is 100V/m~1000V/m) may only or mainly effectively cover the dorsal root ganglion 3 to be stimulated; as greater the distance b (b=4 mm) between the first electrode 121 and the second electrode 122 as shown in FIG. 3B, the field pattern of the electric field is distributed expandingly and completely cover the dorsal root ganglion 3 to be stimulated (the drawn strength of the electric field is 100V/m~1000V/m). Relatively, the electric field strength is more intensive if the position is closer to the electromagnetic field of the first electrode 121 and the second electrode 122. As shown in FIG. 3C, it is a distribution diagram of the field pattern that the field pattern of the electric field in FIG. 3A is applied with a more intensive electric field so the strength of the electric field is distributed in the range 100V/m~5000V/m. From the figure, as long as the electrode is disposed close enough to the target zone which is to be stimulated (the distance c is between 0~10 mm), the electric field has an effect on it and the electric field with higher intensity is distributed more closer to the surface of the electrode. Then, referring to FIG. 3D and FIG. 3E, the difference between FIG. 3D and FIG. 3C is the electrode length a of the first electrode 121 and the second electrode 122. In FIG. 3D, the electrode length a is changed to 2 mm. From FIG. 3D, it is seen that the electrode becomes longer and the space distribution of the field pattern of the electric field also becomes slightly larger. The difference between FIG. 3E and FIG. 3D is that the distance b between the electrodes is changed to 6 mm on the condition that the electrode length a of the first electrode 121 and the second electrode 122 are both fixed (at 2 mm). As the distance b between the electrodes is increased, the space distribution of the field pattern of the electric field also becomes larger.

Figure 4A:
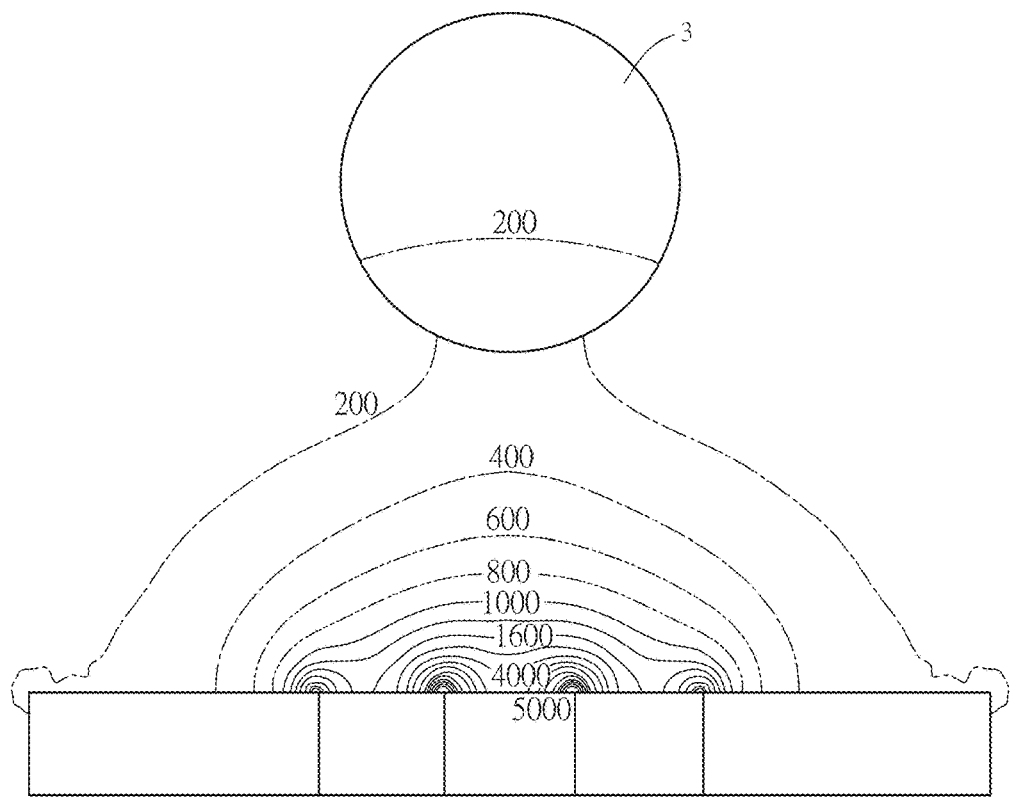
Figure 4B:
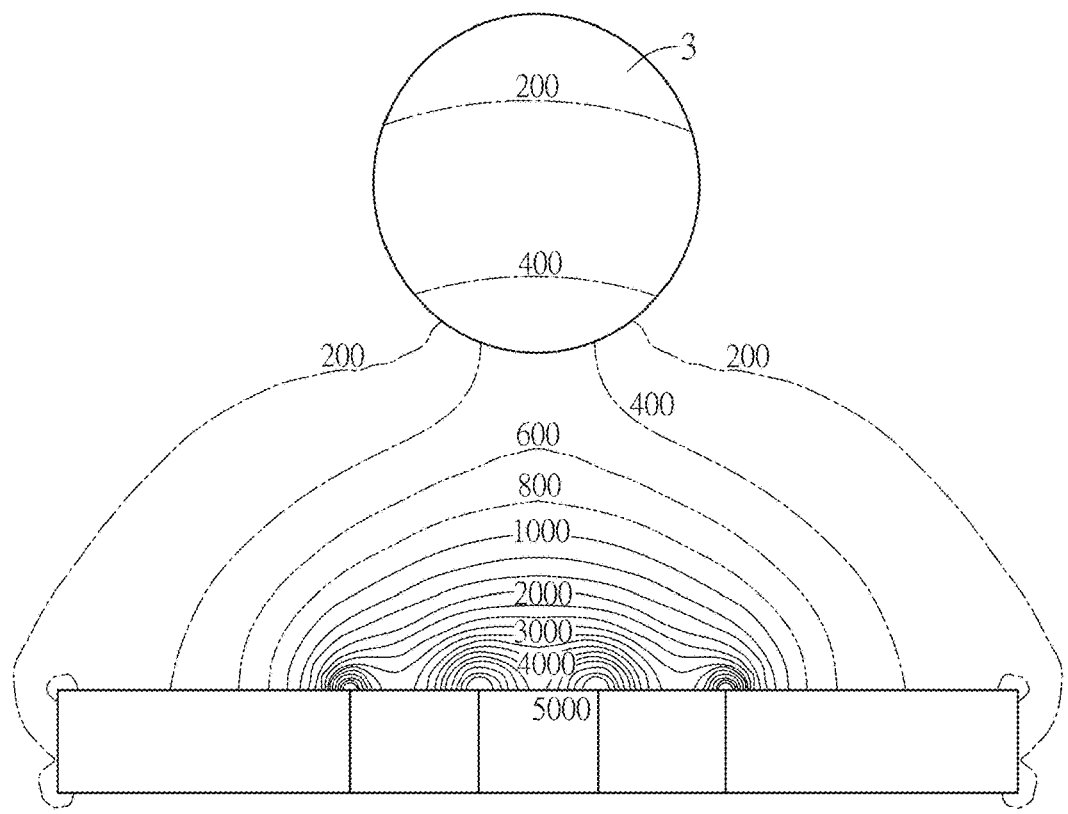
Figure 4C:
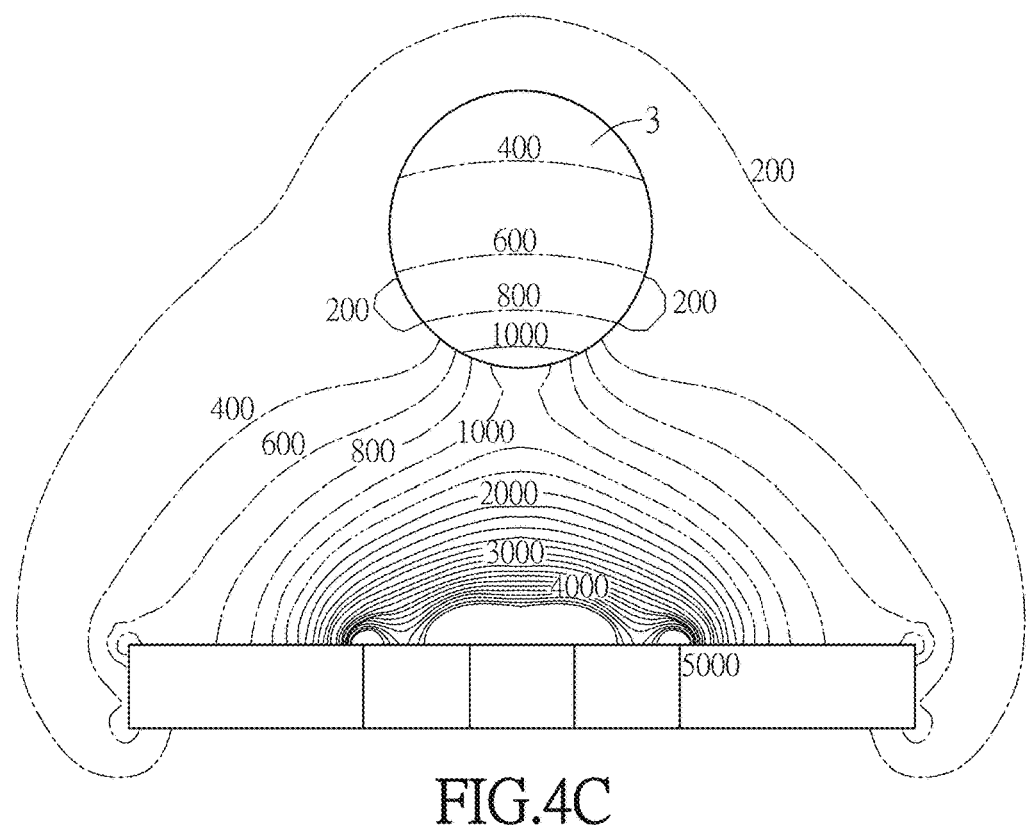

Then, different voltage influences on the space distribution of the field pattern of the electric field are compared. Referring to FIG. 4A to FIG. 4C, the frequency 500 KHz of the constant electrical stimulation signal is applied, and the electrode length a of the first electrode 121 and the second electrode 122, the distance b between the electrodes and the distance c to the target zone to be stimulated are all fixed (a=2 mm, b=2 mm, c=5 mm). Different voltage influences on the space distribution of the field pattern of the electric field are shown in the figures (the voltage is 3V in FIG. 4A, the voltage is 5V in FIG. 4B, the voltage is 10V in FIG. 4C). From the figures, it is seen that as the voltage is greater, the space distribution of the field pattern of the electric field also becomes larger.

Figure 4D:
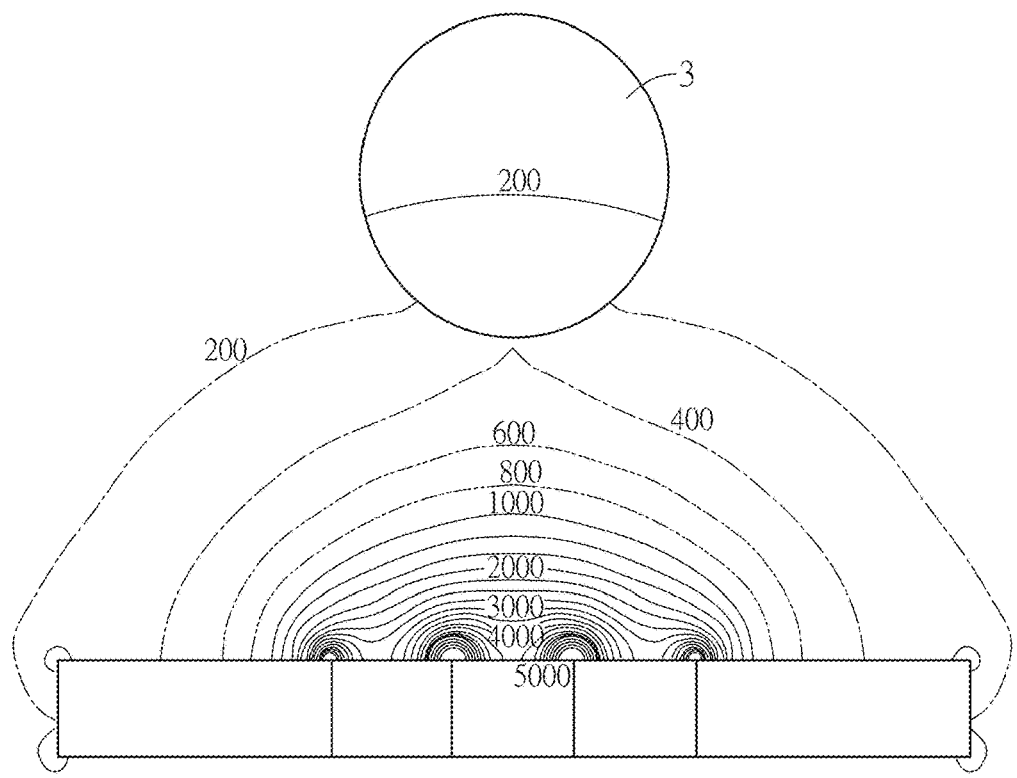
Figure 4E:
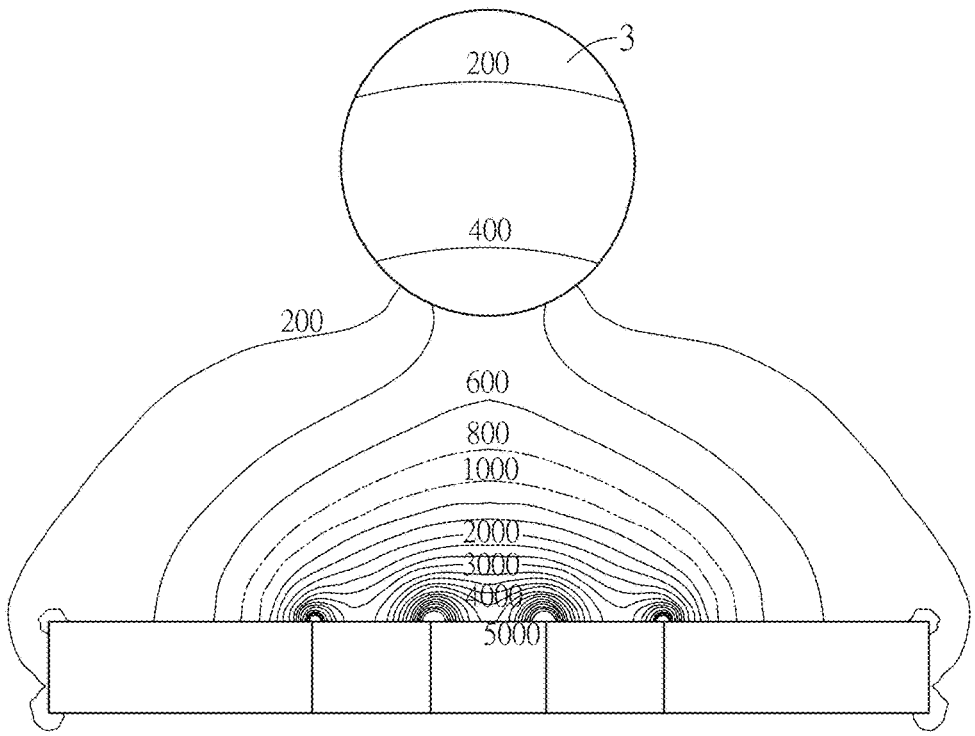

Then, comparing FIG. 4B, FIG. 4D and FIG. 4E, the electrical stimulation signal with 5V is applied, and the electrode length a of the first electrode 121 and the second electrode 122, the distance b between the electrodes, and the distance c to the target zone to be stimulated are all fixed (a=2 mm, b=2 mm, c=5 mm). Different frequency influences of the electrical stimulation signal on the space distribution of the field pattern of the electric field are shown in the figures (the frequency of the electrical stimulation signal is 200 KHz in FIG. 4D, the frequency of the electrical stimulation signal is 500 KHz in FIG. 4B, the frequency of the electrical stimulation signal is 800 KHz in FIG. 4E). From FIG. 5B, because around the arc length at 4 mm it is the point closest to the electronic stimulation unit, the most intensive strength of the electric field is here. As the frequency is increased, the space distribution of the field pattern of the electric field also becomes larger. From FIG. 3A to FIG. 4E, in the embodiment, the electric field strength ranges from 100 V/m to 5000 V/m, preferably from 400 V/m to 5000 V/m.

Figure 5A:
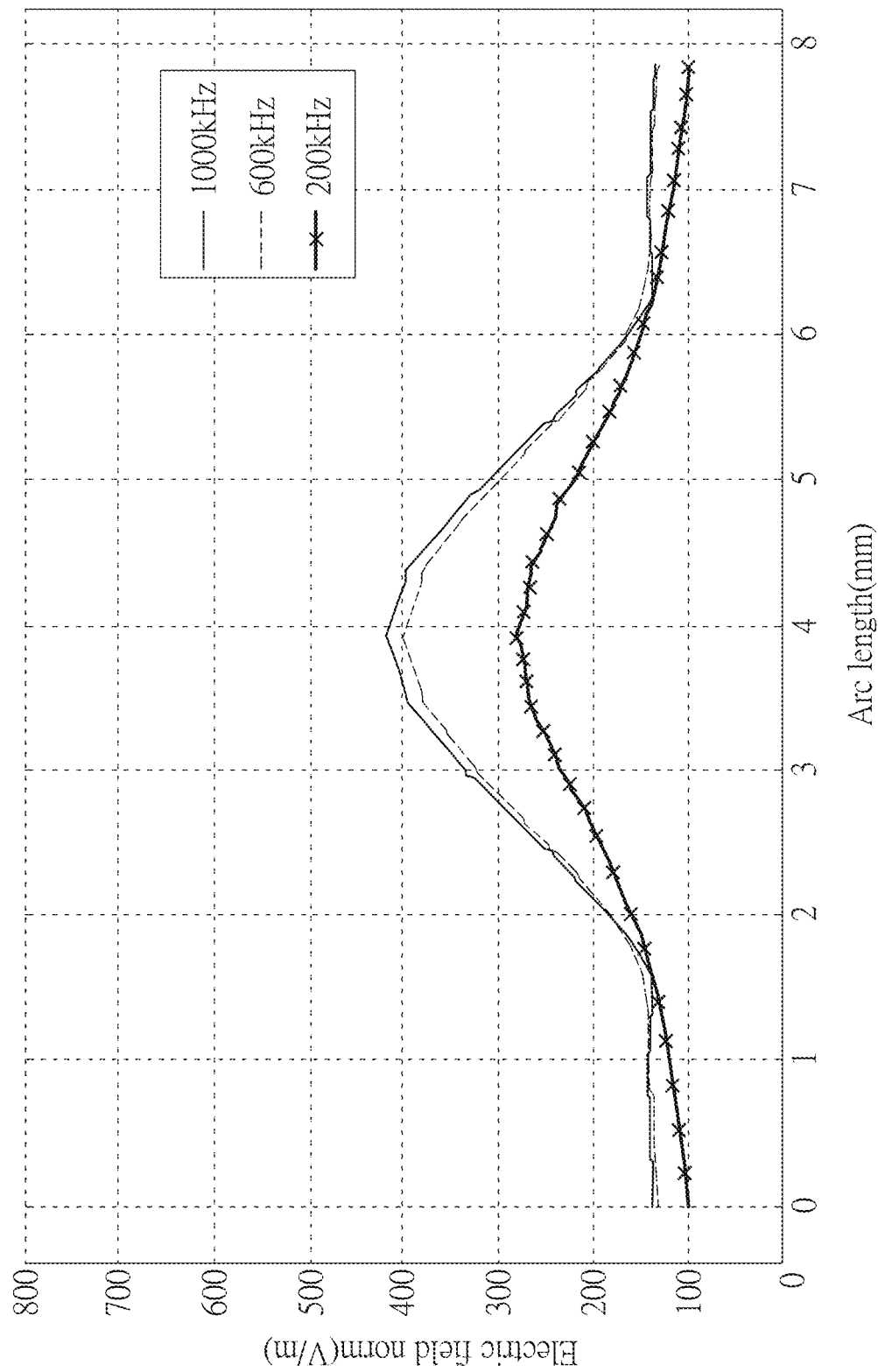
FIG. 5A and FIG. 5B are schematic diagrams of the electric field simulation at the condition that the electronic stimulation device operates at different electrode intervals and different frequencies of the electrical stimulation signals.
Figure 5B:
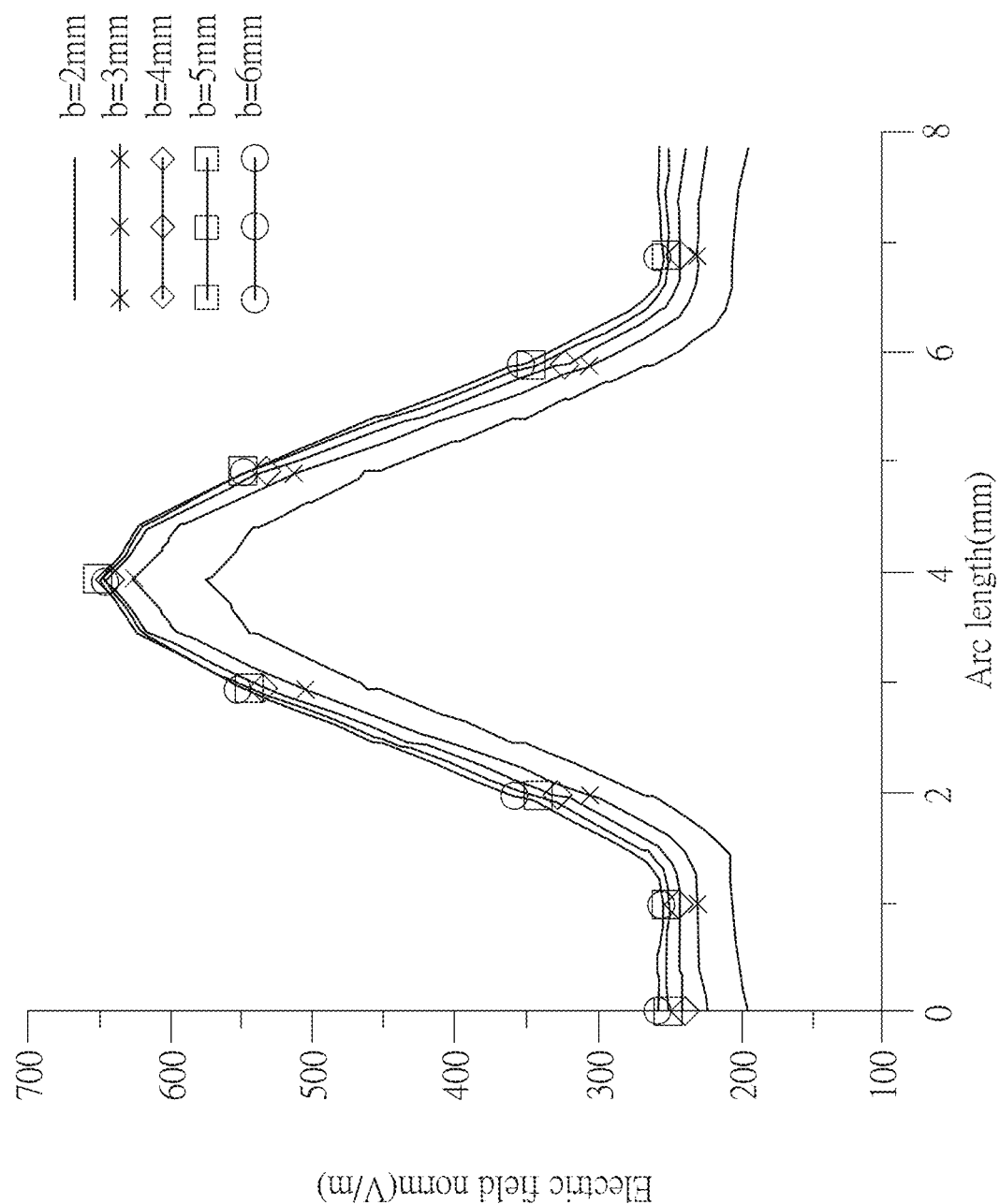

Referring to FIG. 5A and FIG. 5B, the diameter of the target (circular dorsal root ganglion 3) to be stimulated also shown in FIG. 2B is 5 mm, the electrode length a of the first electrode 121 and the second electrode 122 is about 1 mm, the distance c is about 5 mm and the input voltage is 5V. The electric field strength on the target to be stimulated for different arc length location of the electrode (in the horizontal axis, the tangent at the left side of the circle is taken as the start point of the arc 0 mm) is shown in the figures. In FIG. 5A, the corresponding strength of the electric field is detected at different frequencies (200 KHz, 600 KHz and 1000 KHz) for electric stimulation are compared. In FIG. 5B, the corresponding strength of the electric field is detected at different distances b between electrodes (b is 2, 3, 4, 5, or 6 mm.) From FIG. 5A, as the frequency of the electric stimulation signal is increased, the strength of the electric field is more intensive and the space distribution of the field pattern of the electric field also becomes larger. For example, under the condition that the frequency of the electric stimulation signal is 1000 KHz, the maximum strength of the electric field at the target zone may reach 400 V/m. Under the condition that the frequency of the electric stimulation signal is 200 KHz, the maximum strength of the electric field at the target zone may be not intensive enough to reach 300 V/m. From FIG. 5B, if the distance b is between 4 mm~6 mm, the electric field strength of the electromagnetic field reaches its maximum.

In the present embodiment, the range of the above-mentioned electric field that covers the target zone (i.e., the nerve to be stimulated) are calculated by simulation of finite element analysis which is performed by AC/DC module of Comsol Multiphysics™. Before the simulation is performed, the following parameters are required to be inputted: (1) Geometry of the electrodes, including shape, quantity, and dimension (length/width) of the electrode, the distance between two adjacent electrodes, and the distance from the electrode to the to-be-stimulated nerve. The geometry of the electrodes may be obtained by directly loading an established 3D model (ex: a SolidWorks file) into the software. (2) Dielectric properties of mediums, including the conductivities (S/m) and/or permittivities of nerves, muscles, skins and electrodes. (3) Electrical stimulation parameters, including voltages, frequencies and/or pulse widths. With the inclusion of these inputs and simulation, a 2D chart of simulation for electric field established between the electrodes and the to-be-stimulated nerve is obtained, so as to determine the area of the to-be-stimulated nerve covered by the electric field, as well as the respective strength of the electrical field.

After the electronic stimulation unit 12 is implanted in the organism, to utilize it as fully as possible, the electronic stimulation device 1 of the embodiment is able to operate in a low-frequency mode to assist the doctor in checking whether the electrodes are at correct positions after the implantation. For example, in the low-frequency mode, the electronic stimulation unit 12 may deliver a test (low-frequency) electrical stimulation signal of which the frequency is between 0.1 Hz~1 KHz and its pulse width is between 10 µs~500 µs. The electronic stimulation unit 12 delivers the test electrical stimulation signal to stimulate the corresponding motor or sensory nerves so as to check whether the implanted electronic stimulation unit is at the right place to transmit stimulation signals to the motor or sensory nerves at the same region with the target zone. Moreover, the low frequency electrical stimulation signal can be also delivered during the treatment. It means the low frequency electrical stimulation signals are combined with// inserted into the treatment electrical stimulation signals in the same period of time. Thus, there are ultrahigh-frequency (200 KHz~1000 KHz) electrical stimulation signals and low frequency electrical stimulation signals (0.1 Hz~1 KHz) in the same duty cycle.

Figure 6:
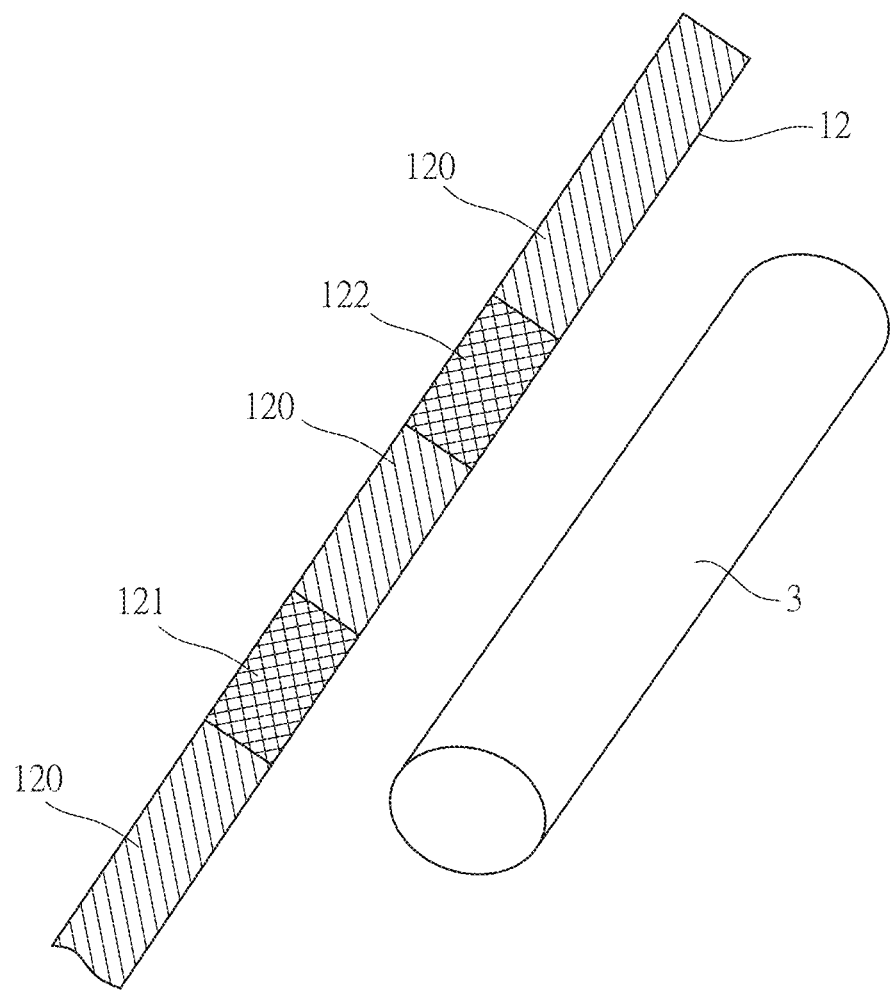
FIG. 6 is another schematic diagram showing the electronic stimulation device in FIG. 1A.

Referring to FIG. 2A and FIG. 6, in the embodiment, the electronic stimulation unit 12 is like a straight line, but it is not limited thereto. The shape of the electronic stimulation unit 12 may be like the shape described in the following embodiments, but it is not limited thereto.

In the embodiment, the electronic stimulation device 1 is an active electronic stimulation device of which the first control unit 11 together with the electronic stimulation unit 12 are implanted in the target zone of the organism. In other words, both the first control unit 11 and the electronic stimulation unit 12 are implanted in the organism subcutaneously. Alternatively, the first control unit 11 and the electronic stimulation unit 12 are integrated into one part first and then implanted subcutaneously. Because of electrically coupled to the controller 2 outside the organism, the first control unit 11 can receive the parameter signal and energy from the second control unit 21 so the electronic stimulation unit 12 may electrically stimulate the target zone of the organism.

Figure 7:
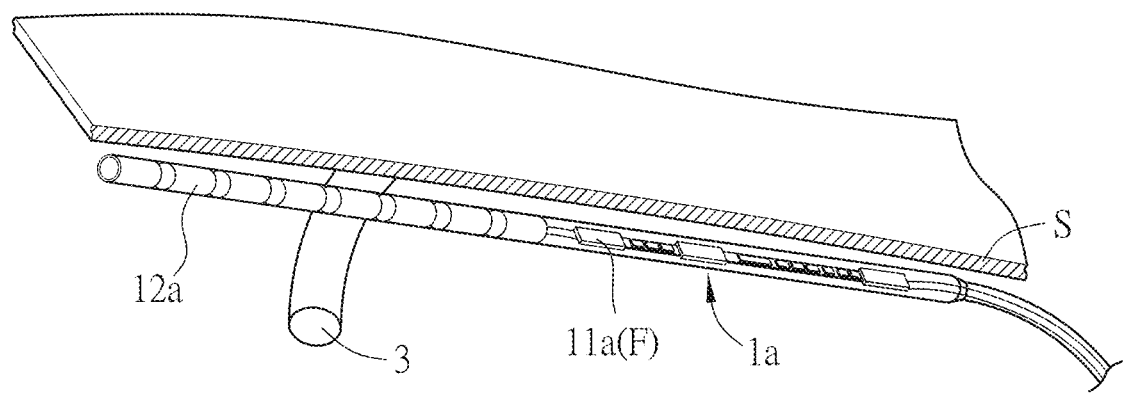
FIG. 7 to FIG. 8 are schematic diagrams showing another examples of the electronic stimulation device according to other embodiments.

The electronic stimulation device of the disclosure is not limited to the electronic stimulation device 1 mentioned above. In other embodiment, the active electronic stimulation device may be like the electronic stimulation device in FIG. 7. The electronic stimulation device 1a in the embodiment and the electronic stimulation device 1 in the previous embodiment have substantially alike elements thereof, and the first control unit 11a and the electronic stimulation unit 12a are also respectively implanted under the epidermis S of the organism (subcutaneous). However in the embodiment, the first control unit 11a of the electronic stimulation device 1a is a FPCB (flexible printed circuit board) integrated in the electronic stimulation unit, and it still can receive the parameter signal and electrical energy from the second control unit (not shown in the figure) outside the organism, and deliver the electrical stimulation signal to the electronic stimulation unit 12a to electrically stimulate the target zone of the organism. In the embodiment, the electronic stimulation device 1a may be narrowed enough to be implanted subcutaneously for abating the burden of the organism (or the patient).

Figure 8:
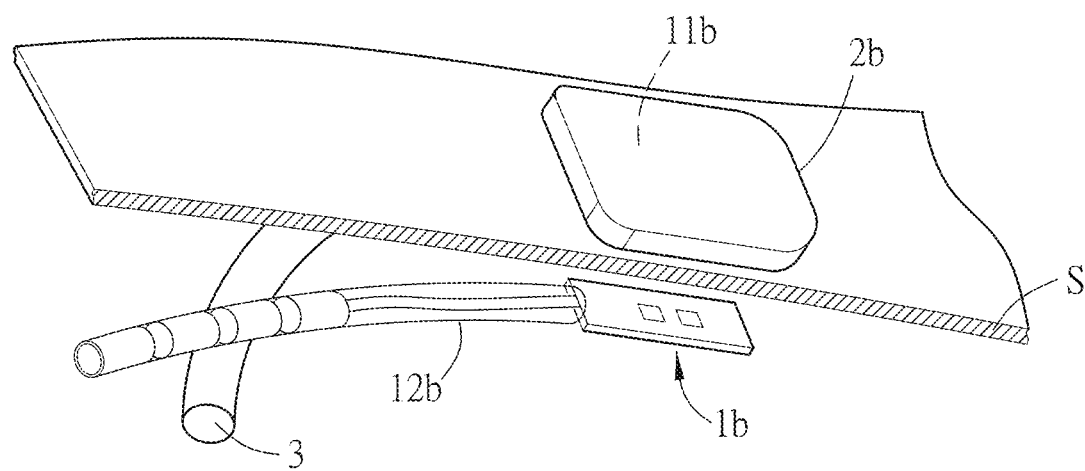

Alternatively, the electronic stimulation device may be like the device shown in FIG. 8. Referring to FIG. 8, in the embodiment, the electronic stimulation device 1b is a passive electronic stimulation device. However, the first control unit 11b of the electronic stimulation device 1b is integrated in the controller 2 outside the epidermis S of the organism (subcutaneous). Thus, the implanted electronic stimulation device 1b does not contain the control unit therein. The electronic stimulation unit 11b (lead) at its end has a FPCB which is implanted subcutaneously and not deeply (for example the depth is less than 5 cm). The controller 2b which is not implanted within the skin can deliver an electrical stimulation signal to the electronic stimulation unit 11b, so the electronic stimulation unit 12b can electrically stimulate the dorsal root ganglion 3 of the organism.

Figure 9:
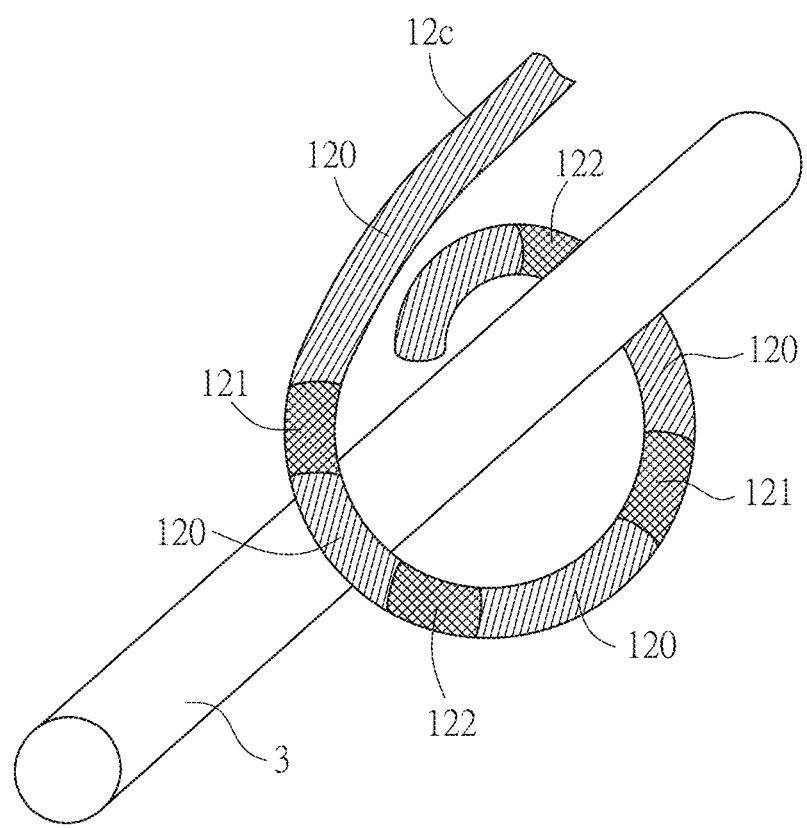
FIG. 9 to FIG. 14 are schematic diagrams showing another examples of the electronic stimulation device.
Figure 12:
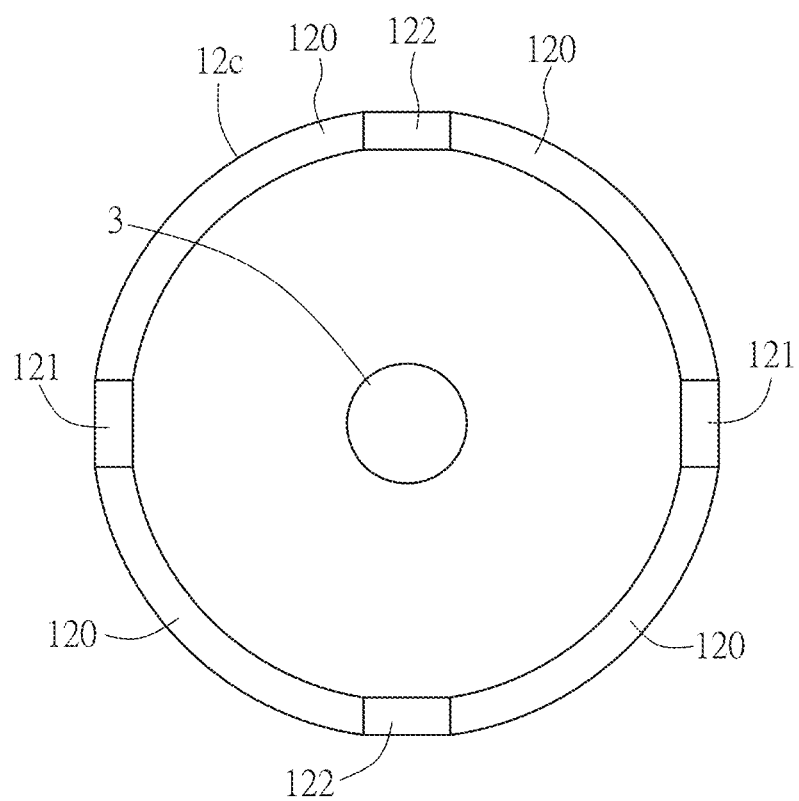
Figure 13:
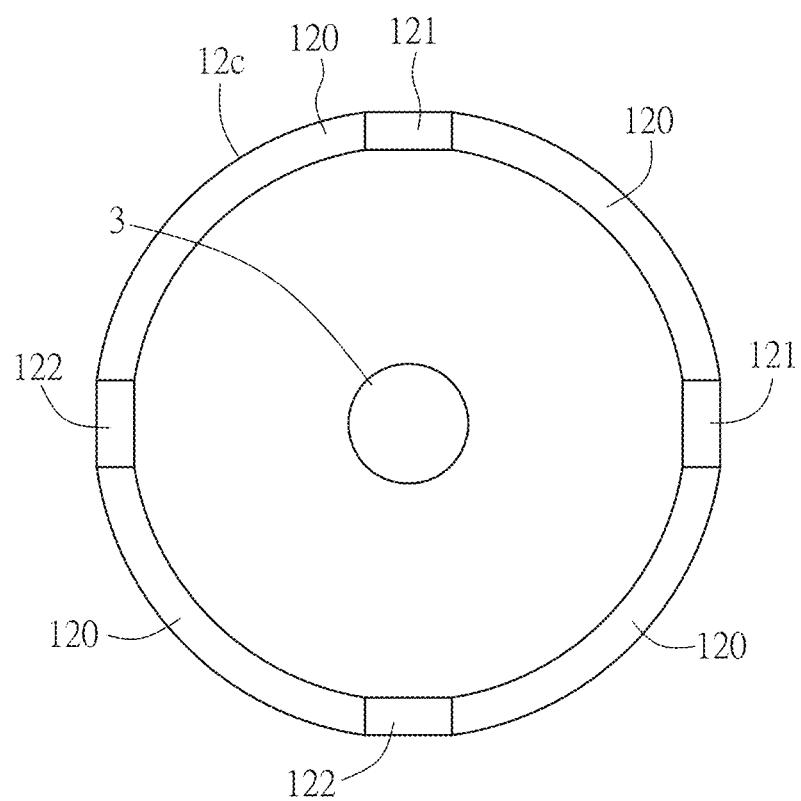
Figure 14:
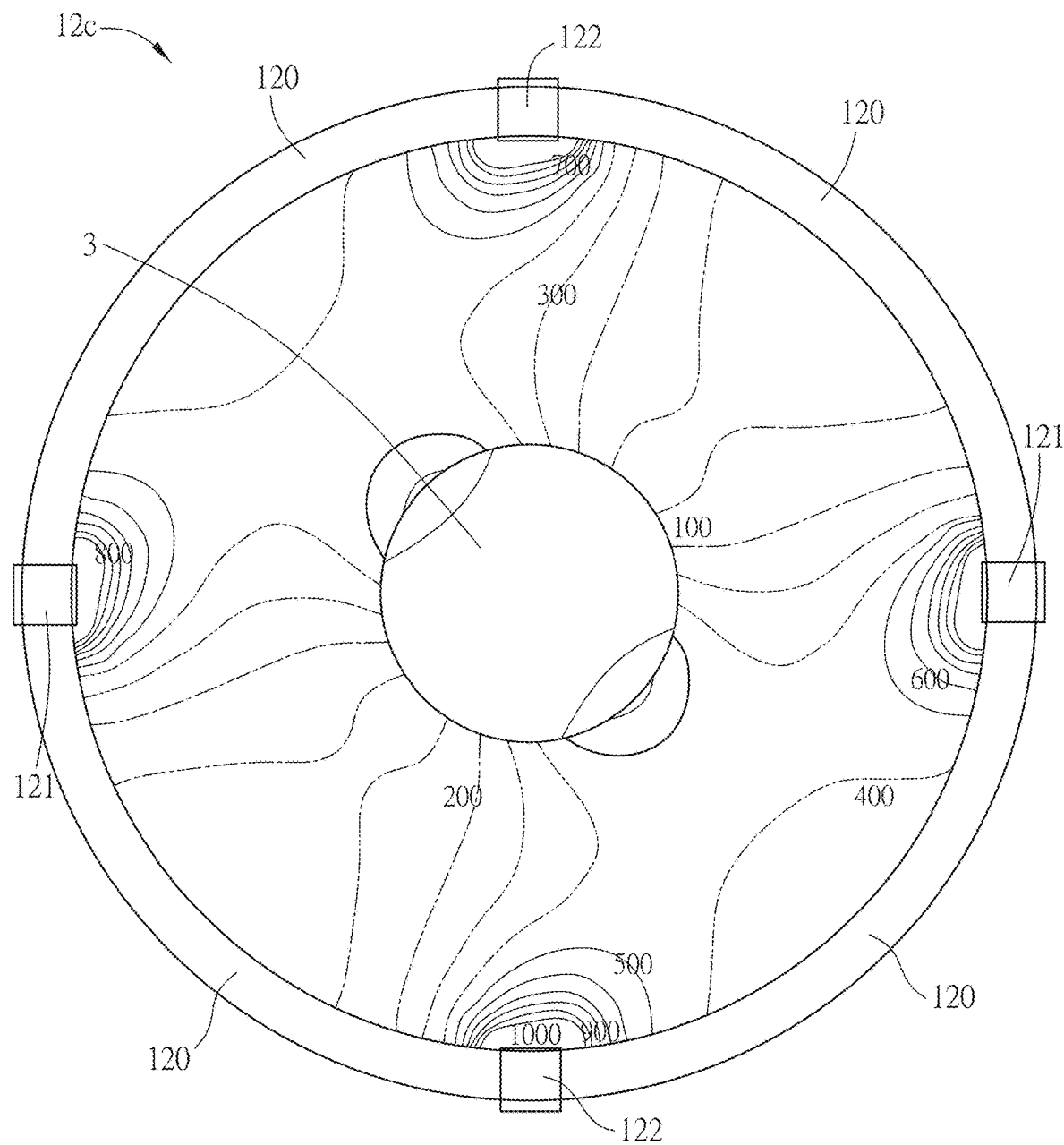

As to implementation of the electronic stimulation unit, it is not limited to the above electronic stimulation unit 12. FIGS. 9, 12, 13 illustrate another embodiment. In the embodiment, the electronic stimulation unit 12c is like a ring, and the electronic stimulation unit 12c includes at least two first electrodes 121 and at least two second electrodes 122. The first electrodes 121 and the second electrode 122 are interlaced at intervals (as shown in FIG. 12). Alternatively, the first electrodes 121 and the second electrodes 122 may be arranged sequentially without interlacement (as shown in FIG. 13). The electric field generated by the first electrode 121 and the second electrode 122 of the electronic stimulation unit 12 surrounds and covers the target dorsal root ganglion 3 (as shown in FIG. 14) to stimulate it with low intensity, low temperature and high frequency electromagnetism. Furthermore, if the position is closer to the first electrode 121 and the second electrode 122, the electric field is more intensive.

Figure 10:
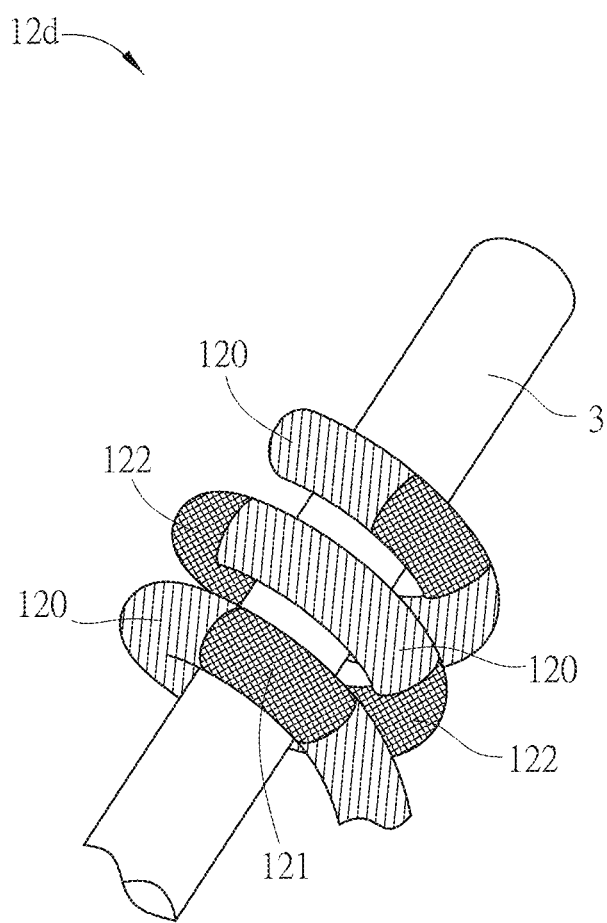

Referring to FIG. 10, the electronic stimulation unit 12d may be like a helix, and the electronic stimulation unit 12d includes at least two first electrodes 121 and at least two second electrodes 122. In the embodiment, the electronic stimulation unit 12d includes two first electrodes 121 and two second electrodes 122 for example. The arrangement of the first electrode 121 and the second electrode 122 is not limited. The first electrodes 121 and the second electrodes 122 may be interlaced or arranged without interlacement, and the first electrodes 121 and the second electrodes 122 may be arranged like a helix to surround the dorsal root ganglion 3. Because the electric field generated by the first electrodes 121 and the second electrodes 122 like a helix surround and cover the target dorsal root ganglion 3, the target dorsal root ganglion 3 is electrically stimulated with low intensity, low temperature and high frequency.

Figure 11:
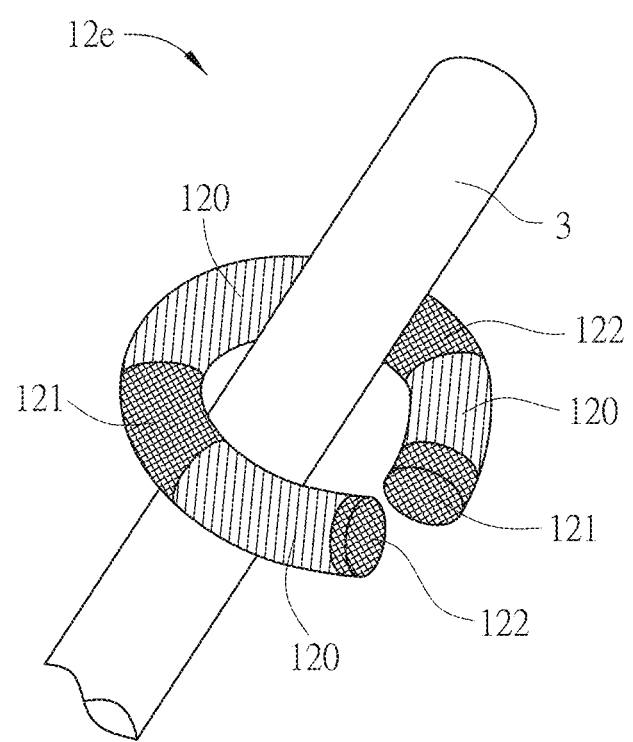

Referring to FIG. 11, in the embodiment, the electronic stimulation unit 12e is like an arc, and the electronic stimulation unit 12e includes at least two first electrodes 121 and at least two second electrodes 122. In the embodiment, the electronic stimulation unit 12e includes two first electrodes 121 and two second electrodes 122 for example. The arrangement of the first electrodes 121 and the second electrodes 122 is not limited. The first electrodes 121 and the second electrodes 122 may be interlaced or arranged without interlacement, and the first electrodes 121 and the second electrodes 122 may be arranged to surround the dorsal root ganglion 3. Because the electric field generated by the first electrode 121 and the second electrode 122 surround and cover the dorsal root ganglion 3, the target dorsal root ganglion 3 is stimulated with low intensity, low temperature and high frequency.

Figure 15:
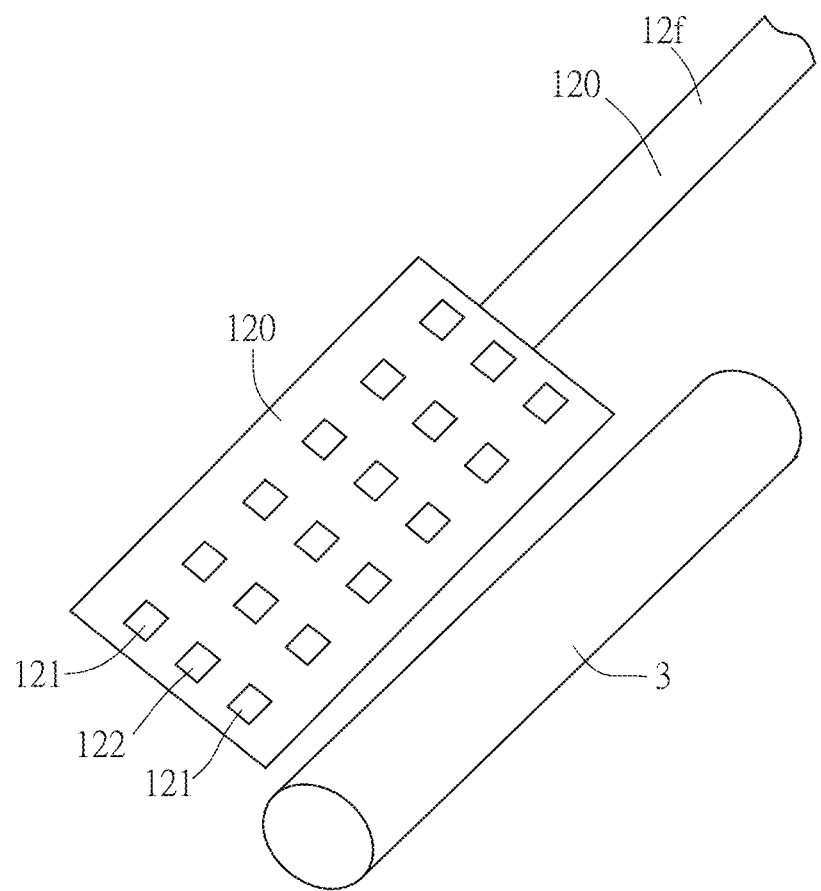
FIG. 15 is a schematic diagrams showing the application of high stimulation device according to an embodiment.

Referring to FIG. 15, in the embodiment, the electronic stimulation unit 12f is like a flake (or a flat), and the electronic stimulation unit 12f includes a plurality of the first electrodes 121 and a plurality of the second electrodes 122. These first electrodes 121 and these second electrodes 122 are arranged at intervals in an array. Similarly, the electric field generated by the first electrode 121 and the second electrode 122 surrounds and covers the dorsal root ganglion 3 so as to electrically stimulate the target, the dorsal root ganglion 3, with low intensity and low temperature.

Please refer to FIGS. 1A, 2A, 18A, 18B, and 18C. In one embodiment of the present disclosure, the electronic stimulation device 1 is provided for electrically stimulating a target zone of an organism. The target zone may be a dorsal root, dorsal horn, spinothalamic tract, Lissauer's tract and a dorsal root entry zone of a spinal cord. The electronic stimulation device 1 comprises at least one electronic stimulation unit 12 (12g). The electronic stimulation unit 12 (12g) includes at least one first electrode 121 and at least one second electrode 122. The electronic stimulation unit 12 delivers an electrical stimulation signal to impel the first electrode 121 and the second electrode 122 to generate an electric field. The range of the electric field covers the target zone, and the electric field strength ranges from 100 V/m to 1000 V/m. At least part of the electronic stimulation unit 12 (12g) is configured to be disposed in a lateral recess of the organism. The electrical stimulation signal delivered by the electronic stimulation device is used to block the neurotransmission in the target zone.

As shown in FIG. 2A, the electronic stimulation unit 12 can comprise a flexible lead and are located at the distal end of the flexible lead. Among these three electrodes, two are the first electrodes 121 and one is the second electrode 122. The second electrode 122 is disposed between the two first electrodes 121. In the present embodiment, the total amount of the electrodes in at least one of the subunits (which are described later) of the electronic stimulation unit 12g is at least three. However, the number of the first and second electrodes may be varied with practical needs, and therefore is not limited herein.

Figure 18A:
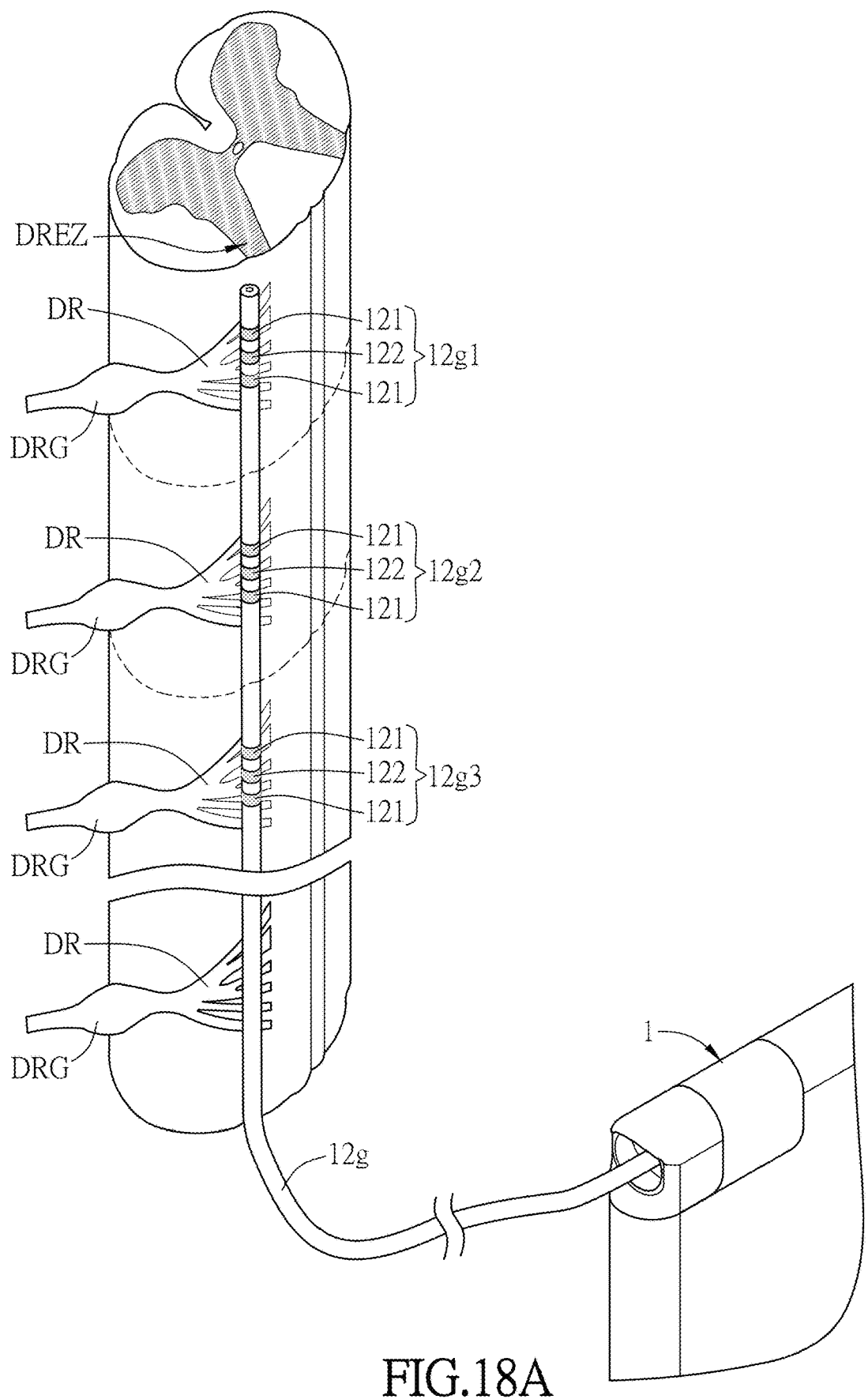
FIGS. 18A and 18C are schematic diagrams showing the electronic stimulation device applied to the lateral recess according to another embodiment.
Figure 18B:
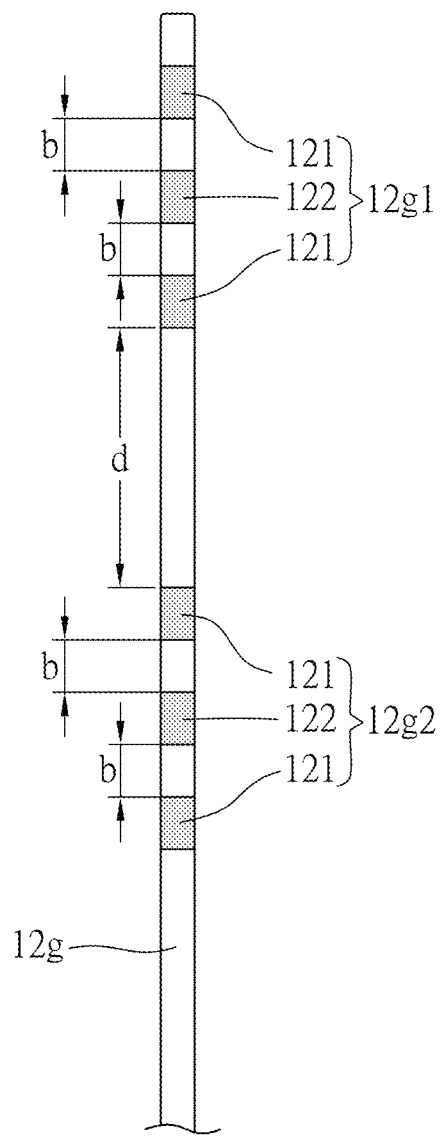
FIG. 18B is an enlarged diagram showing the distal portion of the electronic stimulation unit in FIG. 18A.

As shown in FIGS. 18A and 18B, the electronic stimulation unit 12g of the electronic stimulation device 1 comprises at least two subunits. Here, the amount of the subunits are three: the subunits 12g1, 12g2 and 12g3. Each subunit comprises two first electrodes 121 and one second electrode 122. Similarly, the number of the subunits in the electronic stimulation unit and the number of the electrodes in each subunits both may be varied with practical needs, and therefore are not limited herein. In FIG. 18B, there are only two subunits are shown in the drawing and the third subunit 12g3 is omitted just for clarity. As shown in FIG. 18B, in both the subunits 12g1 and 12g2, each of the first electrodes 121 is separated from the second electrode 122 with a first distance b. In addition, the subunit 12g1 is separated from the subunit 12g2 with a third distance d.

In the present embodiment, the first distance b is smaller than the third distance d. Thus, the distance d between the subunits is for the subunits of electrode to align with the spinal level. The reason why the second distance is not equal to the first distance b is because the electrodes within the lead are compactly arranged to make dense current density or the high electrical field ranging from 100 V/m to 1000 V/m. Due to the compact electrode arrangement, it is no need to use so many electrodes in one lead. Only one subunit is needed for corresponding to one spinal level height and the total amount of the electrodes in one subunits is at least three. The second distance between two different subunits is for separation and saving the electrodes amount. The total length of the electrodes within one subunit is small than one spinal level height. In such configuration, the electronic stimulation device 1 may generate a stronger and more uniformed electrical field to cover the target zone, so that the electronic stimulation device 1 may have a better performance. Moreover, as shown in FIG. 18A, each of the subunits 12g1, 12g2 and 12g3 is configured to be disposed corresponding to one level of the spine (e.g. T8 to T10) of the organism.

Figure 18C:
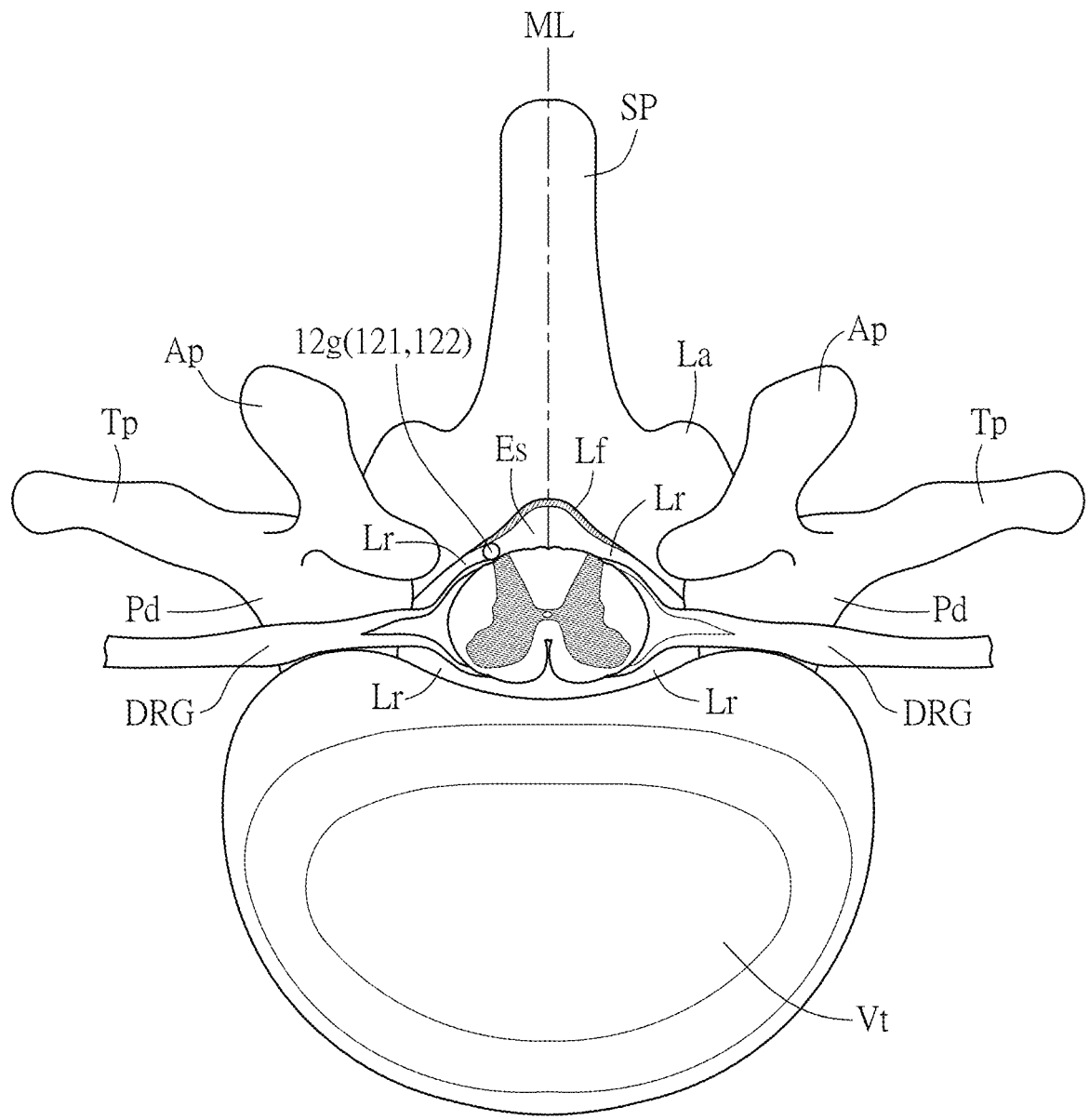

As shown in FIGS. 18A and 18C, the distal portion of the electronic stimulation unit 12g is configured to be disposed in the lateral recess Lr of the organism. As shown in the drawings, the lateral recess Lr is the space within the spinal canal that is located toward the sides, and bordered by the back of the vertebral body Vt (anteriorly), the two pedicles Pd (laterally), the superior articular facets Ap (posteriorly), the transverse processes Tp (posteriorly), laminas La (posteriorly), and ligamentum flavum Lf (posteriorly). In order to generate the electrical field which covers the dorsal root DR, dorsal horn, spinothalamic tract, Lissauer's tract or the dorsal root entry zone DREZ of the spinal cord of the organism, the distal portion of the electronic stimulation unit 12g is preferably disposed in an anatomical space of the posterior part of the lateral recess Lr which is closer, rather than the middle line ML of the spinal process SP, to the dorsal root entry zone DREZ of the spinal cord and the dorsal root DR of the spinal nerve. Also, when the distal portion of the electronic stimulation unit 12g is disposed in the anterior part of the lateral recess Lr, it is preferably disposed in an anatomical space which is closer to the spinothalamic tract of the spinal cord.

It should be appreciated that the anterolateral pathways comprise smaller diameter (i.e., A δ- and C-fibers) axons carrying information about pain and temperature sense. The axons of nociceptive nerve cells enter the spinal cord via the dorsal roots nerves. Axons carrying information from pain (and temperature) receptors are generally found in the most lateral division of the dorsal roots). When these axons reach the dorsal horn, they branch into ascending and descending collaterals, forming the dorsolateral tract of Lissauer. Some axon collaterals will ascend or descend for a few segments in Lissauer's tract before entering the central gray matter. Axons from the second-order sensory neurons in the central gray matter cross over the spinal cord into the anterior commissure to ascend in the anterolateral white matter. In other words, the axons of these second-order sensory neurons cross the midline and ascend all the way to the brainstem and thalamus in the anterolateral quadrant of the contralateral half of the spinal cord. These fibers form part of the spinothalamic tract, which is the major ascending pathway for information about pain and temperature. Therefore, the pathways for pain (and temperature) cross the midline to ascend on the opposite side of the cord, and diminished sensation of pain below the lesion will be observed on the side opposite the lesion. Accordingly, when the electronic stimulation device 1 generate an electrical field which covers the aforementioned target zones, neurotransmissions of the anterolateral pathways may be interrupted, so that the pain sense (as well as the temperature sense, optionally) which is mainly transduced by the anterolateral pathway/spinothalamic tract is also blocked.

Compared with conventional SCS lead implantation procedures, the ultrahigh-frequency (between 200 KHz to 1000 KHz) SCS surgical procedure has a key differences: There is no need for paresthesia testing and programming (paresthesia mapping), while lead implantation. The electrodes of the lead are placed between T8 and T11 (especially T9 and T10, which are target for low limb pain or back pain) level at the epidural space, approximately at the midline or some offset to midline to lateral recess.

The lead positioning for ultrahigh-frequency SCS is straightforward: At least one lead (or only one lead) is placed under fluoroscopic control, and the electrodes are placed between T8 and T11. This not only makes the procedure time predictable and shorter compared with conventional SCS but also allows the use of deep sedation during the whole procedure, making it more comfortable to the patient. Moreover, paresthesia-free stimulation allows for comfortable nighttime use and restoration of sleep quality.

Because configuration, variation or connection relationship to other elements of each detail elements of the electrical stimulation device 1 can refer to the previous embodiments, they are not repeated here.

Moreover, the present disclosure also provides another embodiment, which is a method of treatment applied to electrically stimulate a target zone of an organism by the electronic stimulation device 1 as described above. The electronic stimulation device 1 includes an electronic stimulation unit 11, and the electronic stimulation unit 11 includes at least one first electrode 111 and at least one second electrode 112. The method comprises the following steps: implanting at least part of the electronic stimulation unit 11 in a lateral recess of the organism (Step S01); delivering an electrical stimulation signal by the electronic stimulation unit 11 (Step S02); generating an electric field covering the target zone by the first electrode 111 and the second electrode 112, and the electric field strength ranges from 100 V/m to 1000 V/m (Step S03); and electrically stimulating the target zone (Step S04). The target zone may be a dorsal root, dorsal horn, spinothalamic tract, Lissauer's tract and a dorsal root entry zone of a spinal cord.

Because configuration, variation or connection relationship to other elements of each detail elements of the method can refer to the previous embodiments, they are not repeated here.

Moreover, the present disclosure also provides another embodiment, which is an electronic stimulation system. The electronic stimulation system comprises the controller 2 and the electronic stimulation device 1 as described above. The electronic stimulation device 1 comprises at least one electronic stimulation unit 11. The electronic stimulation unit 11 includes at least one first electrode 111 and at least one second electrode 112. The controller 2 directs the electronic stimulation unit 11 to deliver an electrical stimulation signal to impel the first electrode 111 and the second electrode 112 to generate an electric field. The range of the electric field covers the target zone and the electric field strength ranges from 100 V/m to 1000 V/m for electrically stimulating the target zone. At least part of the electronic stimulation unit 11 is configured to be disposed in a lateral recess.

Because configuration, variation or connection relationship to other elements of each detail elements of the system can refer to the previous embodiments, they are not repeated here.

Figure 19:
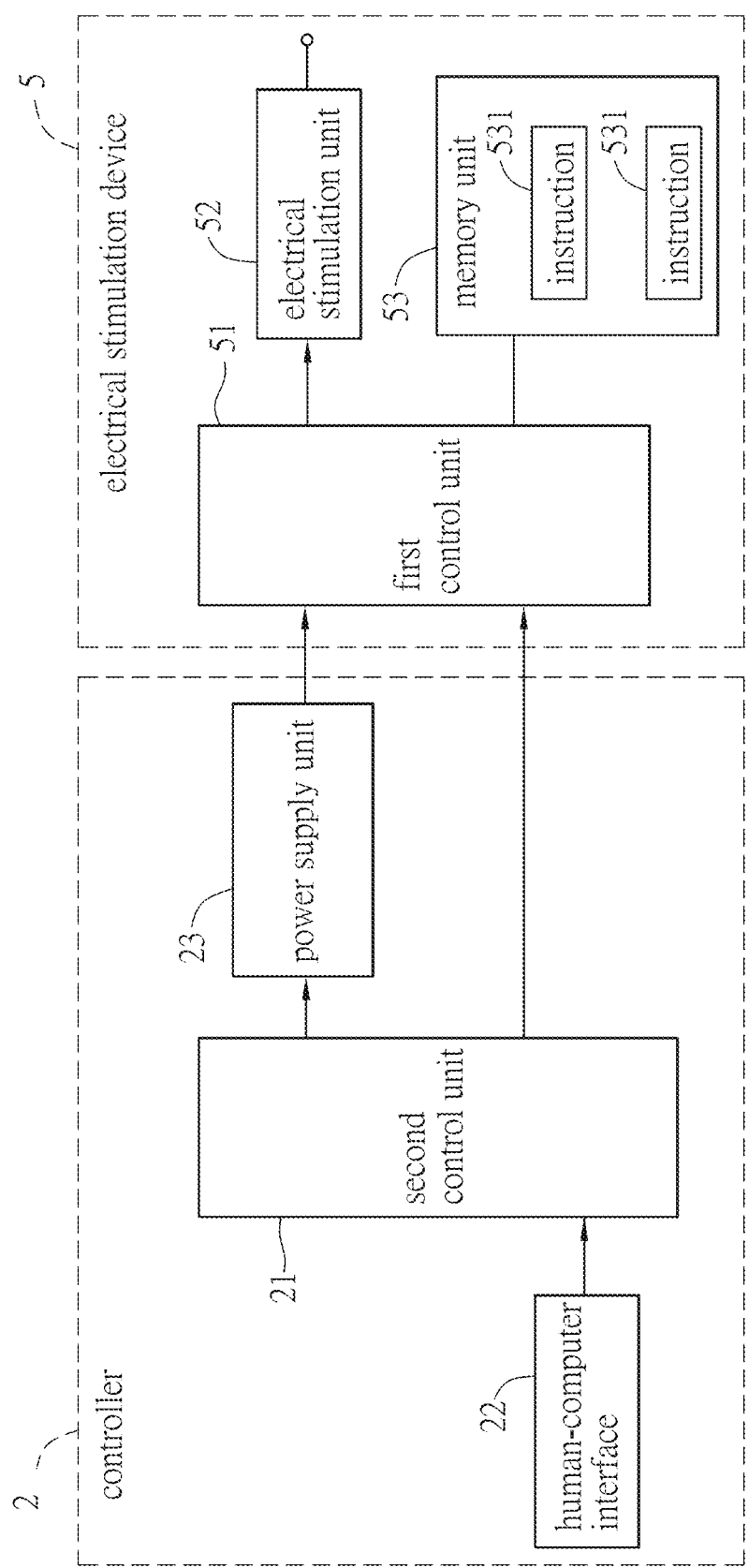
FIG. 19 is a functional block diagram showing the computer-readable medium according to another embodiment.

A computer-readable medium according to still another embodiment of the present invention is also provided. FIG. 19 is a functional block diagram showing the computer-readable medium according to the present embodiment.

The electrical stimulation device 5 also includes a first control unit 51 and an electrical stimulation unit 52. The electrical stimulation unit 52 electrically couples to the first control unit 51. The electrical stimulation device 5 is similar to the electrical stimulation device 1 as described above. The configuration, variation or connection relationship to other elements of each detail elements of the electrical stimulation device 5, as well as the connection relationship to the controller 2, are also substantially the same as those of their corresponding counterparts described in the preceding embodiments. On the other hand, first control unit 51 further electrically couples to a computer-readable medium, which is exemplified as the memory unit 53 in the present embodiment. The memory unit 53 is a non-transitory storage medium, and can be a memory, a memory card, an optical disc drive, a video tape drive, a magnetic tape drive, and/or the combination thereof. The memory can be a ROM, Flash Memory, or Field-Programmable Gate Array (FPGA), or other non-transitory memory.

One or more instructions 531 are stored in the memory unit 53. For the clarity of the figures, two instructions 531 are stored in the memory unit 53 as shown in FIG. 19, but the present invention is not limited thereto. The first control unit 51 can assess the instructions 531 from the memory unit 53, and execute the instructions 531 to control the action of the electrical stimulation device 5. The electrical stimulation device 5 can be applied to electrically stimulate a target zone. The electrical stimulation unit 52 also comprises a first electrode and second electrode.

The instructions 531 are executed by the first control unit 51 to cause the electrical stimulation device 5 to execute an electrical stimulation process, which comprises the following steps: delivering an electrical stimulation signal by the electrical stimulation unit 52 to electrically stimulate the target zone. During the process of the electrical stimulation, an electric field covering the target zone is generated between the first electrode and the second electrode according to the electrical stimulation signal, and a strength of the electric field ranges from 100 V/m to 1000 V/m. At least part of the electronic stimulation unit is configured to be disposed in a lateral recess, such as at least one of the subunit is configured to be disposed in a lateral recess. Moreover, in another embodiment, all of the subunits of the electronic stimulation unit are configured to be disposed in the lateral recess, which is substantially paralleled to the long axial of the spinal cord. As a result, the electrical stimulation signal can partially effect the dorsal ganglion (DRG) and/or the dorsal root nerves, the electric field will also at least partially cover the DRG and/or the dorsal root nerves.

As described above, the present embodiment is exemplified with the electrical stimulation device 5 which is controlled by the first control unit 51 to execute the instructions 531 stored in the memory unit 53 electrically coupled to the first control unit 51. In other words, the electrical stimulation device 5 can independently execute every steps of the electrical stimulation process without any external controller.

In other practicing modes, the computer-readable medium of the present embodiment can be electrically coupled to an external controller (e.g., the controller 2) or a control unit or a CPU of the external controller (e.g., the control unit 21 of the controller 2), to make the electrical stimulation device 5 to execute the steps of the electrical stimulation process. In such practicing mode, the instructions 531 are assessed by the control unit of the external controller to control the electrical stimulation device 5 to deliver the electrical stimulation signal. In other words, the electrical stimulation device 5 and the external controller can be seen as a system, which can execute the instructions stored in the computer-readable medium and the steps of the electrical stimulation process.

Other technical features of the computer-readable medium of the present embodiment can be referred to relevant description of the electrical stimulation device and the controller as described in the above-mentioned embodiments, and they are not repeated here.

From the below experiments, the operation and effect of the electronic stimulation device which stimulates the dorsal root ganglion are explained. However, the below examples are just explanatory but not limited to the scope of the invention.

Experimental Example 1: The Pain Behavior Test on the Foot in the Rat—Von Frey (VF) Test Sprague-Dawley rats (SD rats) of about 275-350 grams weight are used (BioLASCO, Taiwan co., Ltd., Taiwan) and they are provided from the central laboratory animal center of Shin Kong Wu Ho-Su Memorial Hospital. The spinal nerve ligation (SNL) is performed on the L5 spinal nerve of the SD rat. After the development of the pain behavior is stable for few days and conforms to the clinical pain development model, the electronic stimulation unit 1 is implanted and then the high-frequency electrical stimulation therapy is performed. In this experimental example, the rats are divided into the control group (N=3) and the experimental group (N=7) according to the different electrical stimulation treatments. As to the experimental group, the pain behavior is continuously observed for 7 days after surgery. After the pain behavior is stable, the high-frequency electrical stimulation therapy is performed for 5 minutes once a week totally three times, and the responses to the pain behavior tests are observed. The results are shown in FIG. 16.

Figure 16:
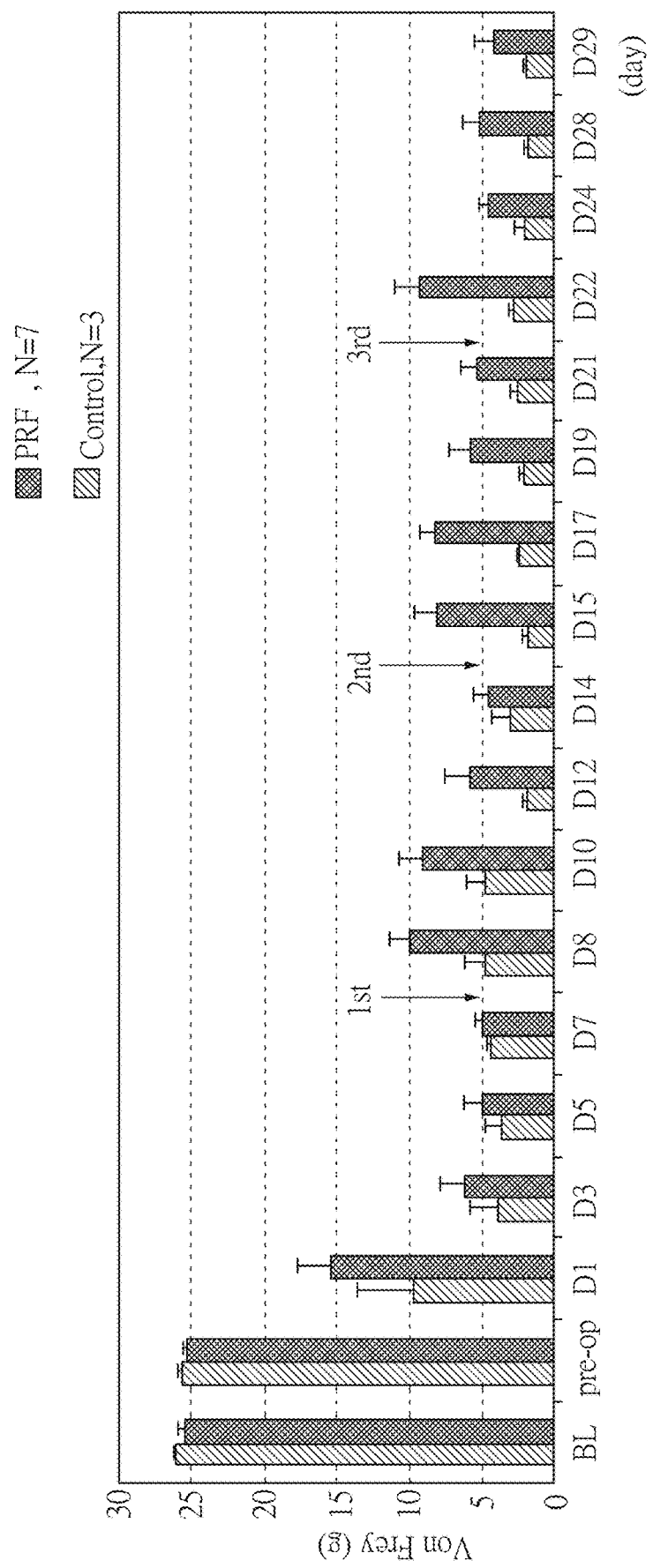
FIG. 16 showing the result of the pain behavior test on the foot in the rat—Von Frey (VF)

As shown in FIG. 16, the pain behavior of the control group becomes stable on the third day until the 29th day, and Von Frey pain pressure thresholds are all less than 5 g (between 1.72±0.39 g and 4.85±1.31 g). As to the experimental group, its pain behavior is similar to that of the control group before receiving high-frequency electrical stimulation therapy (on the 7th day, D7) and becomes stable on about the third day similarly. However, after receiving the first (D7) high-frequency electrical stimulation, its Von Frey pain pressure thresholds are improved. They are different from the control group (D8: 4.73±1.47 g; D10: 4.85±1.31 g) both on D8 (9.85±1.56 g) and D10 (9.0±1.68 g), the tolerance levels of the pressure thresholds in the experimental group are improved up to about 10 g, the pain pressure thresholds increase to about 2.08 times as compared with the control group, and the pain relief will gradually decay until receiving the second high-frequency electrical stimulation therapy (the experimental group D14: 4.53±1.08 g; the control group D14: 2.98±1.44 g). On the next day after receiving the second (D14) high-frequency electrical stimulation therapy (the experimental group D15: 8.12±1.65 g; the control group D15: 1.81±0.53 g; the pain pressure threshold of the experimental group is about 4.49 times greater than that of the control group), the therapy of receiving the first high-frequency electrical stimulation is still effective. The response to the pain behavior test is still excellent on the next day after receiving the third (D21) high-frequency electrical stimulation therapy (the experimental group D22: 9.17±1.93 g; the control group D22: 2.73±0.57 g; the pain pressure threshold of the experimental group is about 3.36 times greater than that of the control group). Obviously, the pain can be immediately relieved, and there are differences of the pain pressure thresholds between the experimental group and the control group every time after receiving the high-frequency electrical stimulation therapy. It approves that after the electrical stimulation unit of the invention is implanted, receiving the high-frequency electrical stimulation therapy for 5 minutes once a week can relieve the pain in a short time.

Experimental Example 2: Neuroelectrophysiological Test

SD rats are divided into the experimental group and the control group, the experimental group (FIG. 17B) receives the high-frequency electrical stimulation for 5 minutes, and the control group (FIG. 17A) does not receive any electrical stimulation. The two groups receive large current stimulation (2.5T, C response threshold) on the sciatic nerve under the same conditions so as to induce obvious A responses (referring to A-fiber) and C responses (referring to C-fiber) occurring in the ipsilateral spinal dorsal horn. Before the interventional measure (high-frequency electrical stimulation for 5 minutes or suspending recording for 5 minutes), the baseline is measured for 30 minutes (18 samples, 100 seconds interval) in advance. After the interventional measure is provided, the large current stimulation is performed on the sciatic nerve once every 30 minutes, the data are continuously recorded for 2 hours, and 5 experimental waveforms are respectively generated in two groups. The results of the control group and the experimental group are respectively shown in FIG. 17A and FIG. 17B.

Figure 17A:
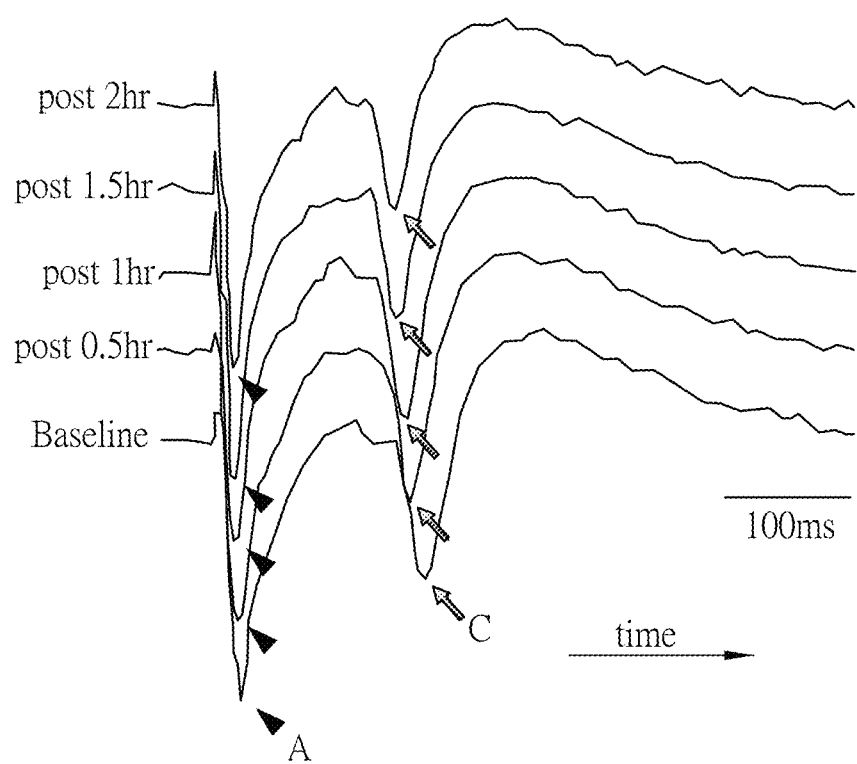
FIG. 17A and FIG. 17B respectively showing the results of the control group and the experimental group of neuro-electrophysiological test.
Figure 17B:
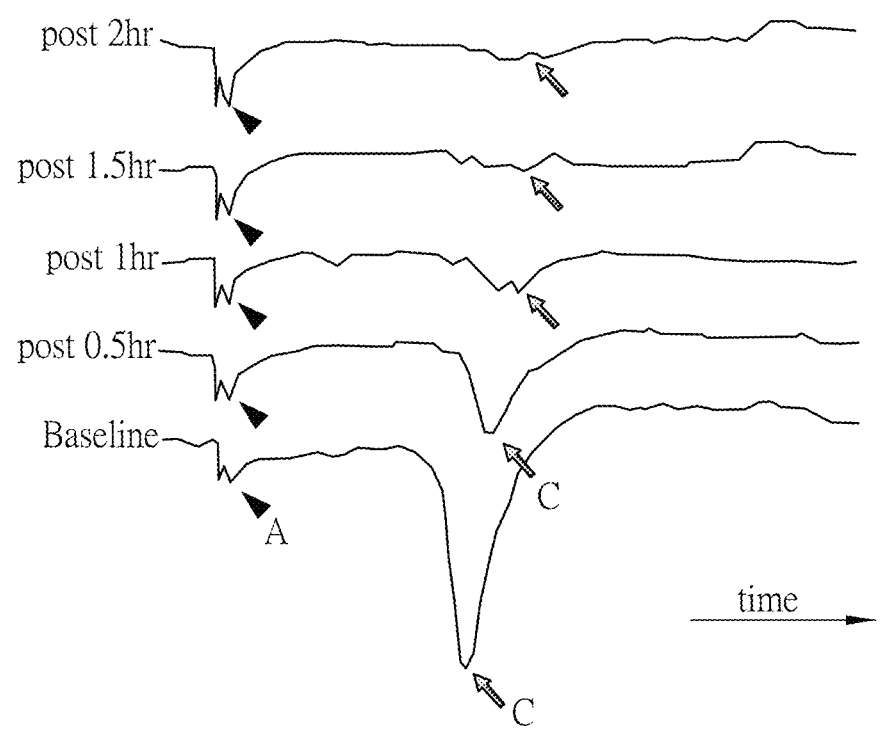

In this experiment, as to the rats receiving the high-frequency electrical stimulation for 5 minutes, the mean values of the neural responses for every 30 minutes are aligned at the point of 90 ms first, and then the individual time of each group are compared. Referring to FIG. 17A and FIG. 17B, the mean lines of interval of every 30 minutes are put together for comparison. Here, there are no significant differences between the curves of individual time in the control group shown in FIG. 17A. Compared with the control group, it can be seen from FIG. 17B that the C-component is relatively largely reduced after the high-frequency electrical stimulation in comparison with the baseline in the experimental group.

In detail, the large current stimulation on the peripheral sciatic nerve acts as the source of pain in this experimental example, and the signal can be transmitted to the dorsal root ganglion and the spinal dorsal root nerves through large diameter nerves (i.e. A-fibers) and small diameter nerves, including myelinated nerve fibers i.e. A δ-fibers) and unmyelinated nerve fibers (i.e. C-fibers) by nerve conduction. The neural response to the interventional measure of high-frequency electrical stimulation can be observed by electrophysiological measurement of nerve conduction. From FIG. 17B, the induced C response is relatively largely reduced with time after receiving the high-frequency electrical stimulation, and the area of the C-component (intensity) is also reduced with time. It shows that the axon of the C-fiber which is responsible for sense of pain (especially the pain which is chronic and difficult to locate) is changed in transmission. The high-frequency electrical stimulation blocks or inhibits the signal transmission of neuron in small diameter fibers or nerves whose transmission velocity is small or equal to 75 m/s, so the pain can be relieved, even totally blocked.

Experimental Example 3: Epidural Neurological Blocking Test

In the present experimental example, Sprague-Dawley rats (SD rats) of about 275-350 grams weight were used (BioLASCO, Taiwan co., Ltd., Taiwan) and provided as described above. The chronic constriction injury (CCI) surgery of rat was conducted as followed. SD rats were anesthetized and their left sciatic nerves were exposed and separated from the surrounding tissues after skin incision at their left thighs and blunt dissection of the biceps femorises. In the experimental group (N=4), the left sciatic nerves of the SD rats were injured by one ligature (chromic gut 4-0 suture). The ligatures were tied loosely around the nerves, but tight enough to cause minor tremors of the calves. The pain behavior of their left hindpaws were tested. The sign of neuropathic pain was expected to exert no later than 5-7 days after surgery. The pain behavior would then become stable, and could remain up to two months. The right hind legs of the same SD rats were not undergone any surgery. The pain behavior of their right hindpaws of the same SD rats were also tested and recorded as the results for control (N=4).

When the pain behaviors of the SD rats became stable (at least 7 days after CCI or sham surgery), electrical leads were implanted in the SD rats as followed. Each SD rat was anesthetized in an acrylic chamber via a mask using 5% isoflurane in air with a flux of 4-8 c.c/min. During the surgery, the concentration of isoflurane was maintained at 2% to 3%, so that the SD rats were anesthetized to unconsciousness without effecting their breathing.

As shown in FIG. 19A, during the operation of the implantation of the electrical lead, two wounds were opened on the back of each SD rat: (1) on the lower back, at T9-T13 level of the spine (distal ends of electrical leads); and (2) on the back neck, at T1 level of the spine (proximal ends of electrical leads).

Positioning of the surgical sites before surgery was facilitated by the bilateral iliums of SD rats. The fictitious straight line connecting the bilateral iliums was perpendicular with the vertebrae at L5 segment. Accordingly, the T13 segment was found by counting the segments along the spine toward the head of the SD rat from L4 segment, and therefore the position of T9-T13 segments was then also found. Some parts of the vertebrae at T9-T13 segments were removed by the method described as followed, so as to place the electrical leads on the epidural space of the SD rat spinal canal.

Please refer to FIGS. 19A and 19B. After the surgical sites were positioned, the posterior approach for thoracic spine (at T9-T13 segments) was performed on SD rats at first. Incision of skin and fascia was carried out along the midline of the thoracic spine, and then muscles were separated from the spinous processes. The gap between the muscles was widen by a retractor, allowing clear visualization of the lamina and until the lamina could be touched by the hand of the operator. The spinous processes and lamina were removed by using a rongeur and Corneoscleral Punch to form an opening with a size of 3 cm in length and 2 cm in width. The spinous processes and lamina were remove until the epidural space could be observed from the opening but the overall structure of the vertebra still remained substantially intact.

Later, a small wound was opened on the back neck of the SD rat, at T1 segment of the spine. A subcutaneous tunnel was formed from the wound at the T1 segment to the wound at T9-T13 segments by using hemostatic forceps to separate the skin from the fascia. The electrical lead was winded to an appropriate length. Stainless steel wires were used to fix the winded portion of the electrical leads to form loops, so that the lead would not be easy to be moved in the SD rat by stretch after implantation. A silicon anchor was tied to each the proximal and distal ends of the electrical lead. The loops of the electrical leads were stuffed into and then fixed in the subcutaneous tunnel of the rat. The proximal and distal ends of the electrical leads was positioned at the T1 segment and the T9-T13 segments, respectively. The silicon anchors tied on the proximal and distal ends of the electrical leads were stitched on the subcutaneous tissue with chromic gut 4-0 sutures. The distal end of the electrical lead was fixed on the aforementioned opening (3 cm in length×2 cm in width) by the bilateral supraspinous ligaments. At last, the proximal end of the electrical lead was protruded from the skin at the back neck (T1 segment) of the SD rat and connected with an external electrical stimulation system. After both ends of the electrical lead were fixed, the fascia and the skin of the SD rat were stitched successively. The electrical lead implanted in the rat comprised 4 electrodes, two first electrodes and two second electrodes, at the proximal end. Each electrode was 2 mm in width and separated from each other with an interval of 2 mm.

On the 7th day after the implantation of the electrical leads, each SD rat received the electrical stimulation for 5 minutes. The frequency of the electrical stimulation signal was 500 KHz. The duration time Td of the pulses in single pulse period was 20 milliseconds. The preset voltage applied across the first electrode and the second electrode was +10V, and pulse-repetition frequency (PRF) was 2 Hz.

The mechanical threshold was evaluated using a dynamic plantar aesthesiometer (UGO 34750, UGO BASILE S.r.l, Italy). In brief, the left hind paw of each animal was pressed using von Frey fibers with incremental strength (0-26.0 g, slew rate of 2 gram/sec) onto the plantar surface. Von Frey tests were performed on the SD rats at following time points: before CCI or sham surgery (BL), on every day after CCI or sham surgery (CCI D1 to CCI D7), on every day after implantation of the electrical leads (Lead D1 to Lead D6), 30 minutes on the first day (day 0) after receiving electrical stimulation (PRF D0), 24 hours after receiving electrical stimulation (PRF D1), on days 5 and 8 after receiving electrical stimulation (PRF D5 and D8). The results are shown in FIG. 20.

Figure 20:
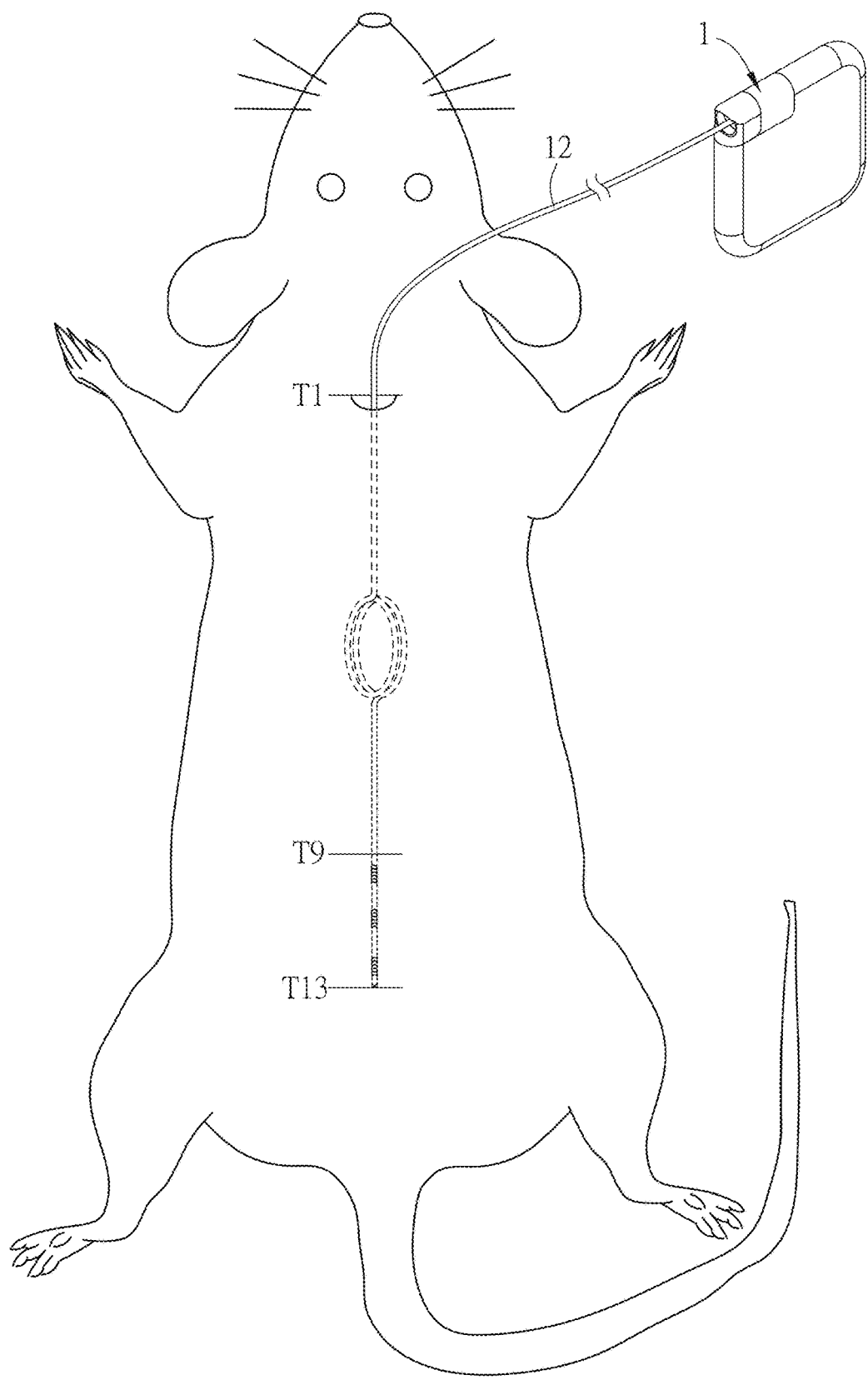
FIG. 20 is a schematic diagram showing the electronic stimulation unit applied to the SD rat according to the experimental example 3 of the present disclosure.
Figure 21:
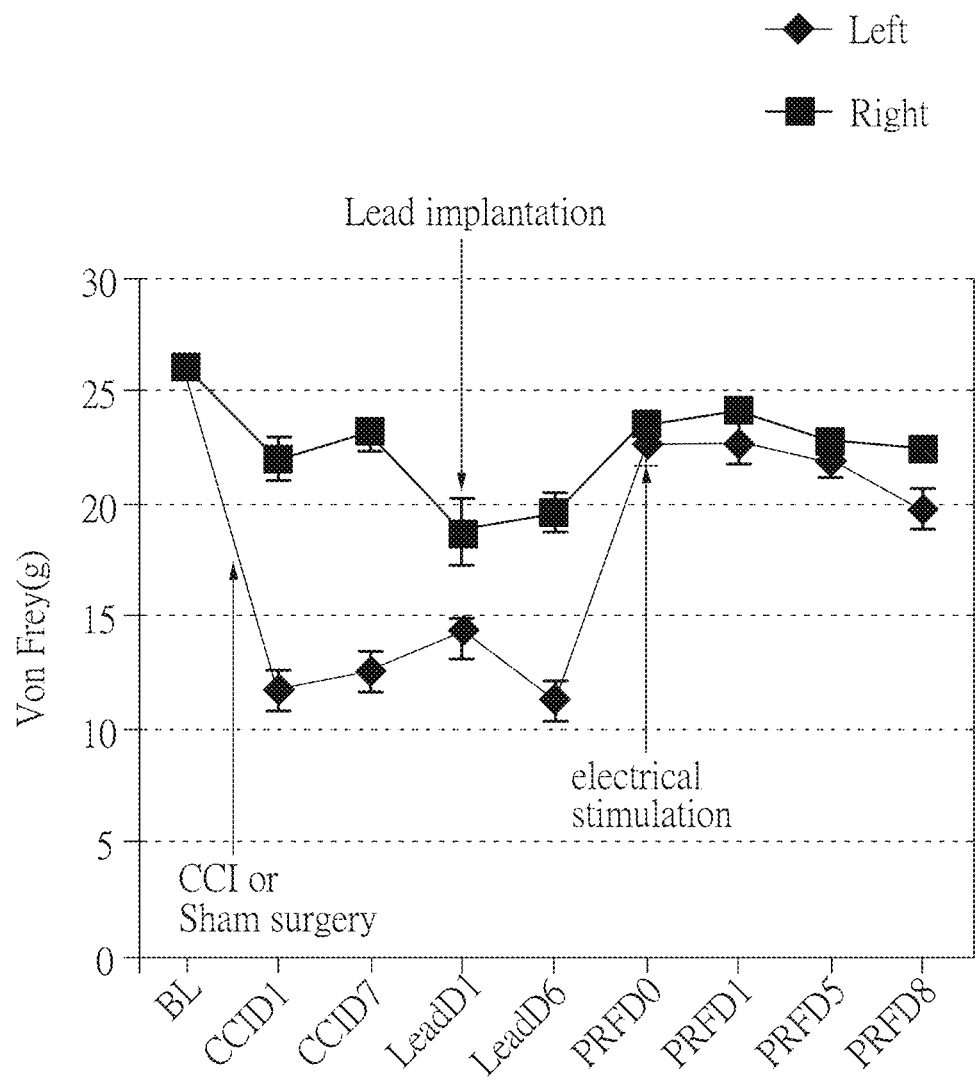
FIG. 21 depicts the results of the experimental example 3 of the present disclosure.

The effect of the PRF stimulation on CCI-induced mechanical allodynia are shown in FIG. 20. According to the results as shown in FIG. 20, CCI resulted in drastically mechanical hypersensitivities. The sign of neuropathic pain was exerted on day 1 after CCI (CCI D1) whereas it was not shown in the control group. The pain behavior of the experimental group remained stable until the day receiving PRF electrical stimulation (CCI D1 to Lead D6). After receiving PRF electrical stimulation, the pain was alleviated in a short time 30 minutes (PRF D0). The effect of pain relief remained for 24 hours after the PRF electrical stimulation (PRF D0 to PRF D1). In addition, the efficacy of the PRF electrical stimulation lasted for about one week after the PRF electrical stimulation (PRF D1 to PRF D8).

Moreover, from the results shown in the present experimental example and the Experimental examples 1 and 2, the electrical stimulation of the present embodiment will not damage to the nerve(s) to be stimulated whereas such electrical stimulation can relieve the pain within a short time (no longer than 20 minutes per day) and the efficacy may lasted for as long as 30 minutes, 24 hours, or even up to about one week.

In summary, with only one shot of the electrical stimulation of the present embodiment, the effect of the electrical stimulation provided by the present embodiment can last at least for 24 hours, and even for 7 days after receiving the electrical stimulation. Obviously, the pain can be effectively relived by the PRF electrical stimulation of the present embodiment with a prolonged effect.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An electronic stimulation device for electrically stimulating a target zone of an organism, comprising:
    at least one electronic stimulation unit including at least one first electrode and at least one second electrode, wherein at least part of the electronic stimulation unit is configured to be disposed in a lateral recess to deliver an electrical stimulation signal to impel the first electrode and the second electrode, so as to generate an electric field, which covers the target zone, and the electric field strength ranges from 100 V/m to 1000 V/m,
    wherein the electronic stimulation unit configured to be disposed in the lateral recess blocks or inhibits the signal transmission of neuron in small diameter fibers or nerves whose transmission velocity is smaller than or equal to 75 m/s.

2. The electronic stimulation device according to claim 1, wherein the frequency of the electrical stimulation signal ranges from 200 KHz to 1000 KHz.

3. The electronic stimulation device according to claim 1, wherein the electronic stimulation unit comprises a plurality of subunits and each subunit comprises at least one first electrode and at least one second electrode.

4. The electronic stimulation device according to claim 3, wherein in each subunit the first electrode is separated from the second electrode with a first distance, and each subunit is separated from each other in a second distance, and the first distance is smaller than the second distance.

5. The electronic stimulation device according to claim 3, wherein the total amount of the subunits is at least three.

6. The electronic stimulation device according to claim 3, wherein each subunit is configured to be disposed corresponding to one level of the spine of the organism.

7. The electronic stimulation device according to claim 1, wherein the target zone is selected from the group consisting of a dorsal root, dorsal horn, spinothalamic tract, Lissauer's tract and a dorsal root entry zone of a spinal cord.

8. The electronic stimulation device according to claim 1, wherein the electronic stimulation unit comprises a lead including at least one first electrode and at least one second electrode and the distal lead tip is configured to be disposed between T8 and T10.

9. A method of treatment applied to electrically stimulate a target zone of an organism by an electronic stimulation device, wherein the electronic stimulation device includes an electronic stimulation unit including at least one first electrode and at least one second electrode, comprising:
    implanting at least part of the electronic stimulation unit in a lateral recess of the organism;
    delivering an electrical stimulation signal by the electronic stimulation unit;
    generating an electric field covering the target zone by the first electrode and the second electrode, wherein the electric field strength ranges from 100 V/m to 1000 V/m; and
    electrically stimulating the target zone, wherein the electronic stimulation unit configured to be disposed in the lateral recess blocks or inhibits the signal transmission of neuron in small diameter fibers or nerves whose transmission velocity is smaller than or equal to 75 m/s.

10. The method according to claim 9, wherein the frequency of the electrical stimulation signal ranges from 200 KHz to 1000 KHz.

11. The method according to claim 9, wherein the electronic stimulation unit comprises a plurality of subunits and each subunit comprises at least one first electrode and at least one second electrode.

12. The method according to claim 11, wherein in each subunit the first electrode is separated from the second electrode with a first distance, and each subunit is separated from each other in a second distance, and the first distance is smaller than the second distances.

13. The method according to claim 11, wherein the total amount of the subunits is at least three.

14. The method according to claim 11, wherein each subunit is configured to be disposed corresponding to one level of the spine of the organism.

15. The method according to claim 9, wherein the target zone is selected from the group consisting of a dorsal root, dorsal horn, spinothalamic tract, Lissauer's tract and a dorsal root entry zone of a spinal cord.

16. The method according to claim 9, wherein the electronic stimulation unit comprises a lead including at least one first electrode and at least one second electrode and the distal lead tip is configured to be disposed between T8 and T10.

17. An electronic stimulation system, comprising:

a controller; and an electronic stimulation device comprising at least one electronic stimulation unit including at least one first electrode and at least one second electrode, wherein at least part of the electronic stimulation unit is configured to be disposed in a lateral recess, the controller directs the electronic stimulation unit to deliver an electrical stimulation signal to impel the first electrode and the second electrode so as to generate an electric field, which covers the target zone and the electric field strength ranges from 100 V/m to 1000 V/m for electrically stimulating the target zone, wherein the electronic stimulation unit configured to be disposed in the lateral recess blocks or inhibits the signal transmission of neuron in small diameter fibers or nerves whose transmission velocity is smaller than or equal to 75 m/s.

18. The electronic stimulation system according to claim 17, wherein the frequency of the electrical stimulation signal ranges from 200 KHz to 1000 KHz.

19. The electronic stimulation system according to claim 17, wherein the electronic stimulation unit comprises a plurality of subunits and each subunit comprises at least one first electrode and at least one second electrode.

20. The electronic stimulation system according to claim 19 wherein in each subunit the first electrode is separated from the second electrode with a first distance, and each subunit is separated from each other in a second distance, and the first distance is smaller than the second distance.

21. The electronic stimulation system according to claim 19, wherein the total amount of the subunits is at least three.

22. The electronic stimulation system according to claim 19, wherein each subunit is configured to be disposed corresponding to one segment of the spine of the organism.

23. The electronic stimulation system according to claim 17, wherein the target zone is selected from the group consisting of a dorsal root, dorsal horn, spinothalamic tract, Lissauer's tract and a dorsal root entry zone of a spinal cord.

24. The electronic stimulation device according to claim 17, wherein the electronic stimulation unit comprises a lead including at least one first electrode and at least one second electrode and the distal lead tip is configured to be disposed between T8 and T10.

* * * * *